(12) United States Patent
Archer et al.

(10) Patent No.: US 8,535,894 B2
(45) Date of Patent: Sep. 17, 2013

(54) ANTIBODY COMPLEXES AND METHODS FOR IMMUNOLABELING

(75) Inventors: Robert Archer, Eugene, OR (US);
Richard Haugland, Eugene, OR (US);
Rosaria Haugland, Eugene, OR (US);
Joseph Beechem, Eugene, OR (US);
David Hagen, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/610,009

(22) Filed: Sep. 11, 2012

(65) Prior Publication Data
US 2013/0072666 A1    Mar. 21, 2013

Related U.S. Application Data

(60) Division of application No. 12/047,131, filed on Mar. 12, 2008, now Pat. No. 8,304,195, which is a continuation of application No. 10/467,550, filed as application No. PCT/US02/31416 on Oct. 2, 2002, now abandoned, which is a continuation of application No. 10/118,204, filed on Apr. 5, 2002, now Pat. No. 8,323,903.

(60) Provisional application No. 60/369,418, filed on Apr. 1, 2002, provisional application No. 60/329,068, filed on Oct. 12, 2001.

(51) Int. Cl.
*G01N 33/53* (2006.01)

(52) U.S. Cl.
USPC ............................................. 435/7.1; 436/518

(58) Field of Classification Search
None
See application file for complete search history.

(56) References Cited

U.S. PATENT DOCUMENTS

| 3,996,345 | A | 12/1976 | Ullman et al. |
| 4,174,384 | A | 11/1979 | Ullman et al. |
| 4,196,265 | A | 4/1980 | Koprowski et al. |
| 4,199,559 | A | 4/1980 | Ullman et al. |

(Continued)

FOREIGN PATENT DOCUMENTS

| EP | 0150905 A2 | 8/1985 |
| EP | 0178125 | 4/1986 |

(Continued)

OTHER PUBLICATIONS

*Pierce Biotechnology Product Literature*, Sep. 30, 2002, 4 pages.

(Continued)

*Primary Examiner* — Jacob Cheu

(57) ABSTRACT

Provided are labeling reagents and methods for labeling primary antibodies and for detecting a target in a sample using an immuno-labeled complex that comprises a target-binding antibody and one or more labeling reagents. The labeling reagents comprise monovalent antibody fragments or non-antibody monomeric proteins whereby the labeling proteins have affinity for a specific region of the target-binding antibody and are covalently attached to a label. Discrete subsets of labeling reagent and immune-labeled complexes are provided that facilitate the simultaneous detection of multiple targets in a sample-complexes are distinguished by i) a ratio of label to labeling reagent, or ii) a physical property of said label, or iii) a ratio of labeling reagent to said target-binding antibody, or iv) by said target-binding antibody. This is particularly useful for fluorophore labels that can be attached to labeling reagents and subsequently immuno-labeled complexes in ratios for the detection of multiple targets.

9 Claims, 7 Drawing Sheets

(56) References Cited

U.S. PATENT DOCUMENTS

| | | |
|---|---|---|
| 4,235,869 A * | 11/1980 | Schwarzberg ............... 436/512 |
| 4,261,968 A | 4/1981 | Ullman et al. |
| 4,384,042 A | 5/1983 | Miike et al. |
| 4,469,787 A | 9/1984 | Woods et al. |
| 4,481,298 A | 11/1984 | Cone, Jr. et al. |
| 4,520,110 A | 5/1985 | Stryer et al. |
| 4,542,104 A | 9/1985 | Stryer et al. |
| 4,603,290 A | 7/1986 | Shinomiya et al. |
| 4,642,334 A | 2/1987 | Moore et al. |
| 4,659,678 A | 4/1987 | Forrest et al. |
| 4,661,444 A | 4/1987 | Li et al. |
| 4,665,024 A | 5/1987 | Mansour et al. |
| 4,714,763 A | 12/1987 | Theodoropulos |
| 4,737,579 A | 4/1988 | Hellstrom et al. |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,868,109 A | 9/1989 | Lansdorp |
| 4,891,313 A | 1/1990 | Berger et al. |
| 4,945,171 A | 7/1990 | Haugland et al. |
| 4,946,778 A | 8/1990 | Ladner et al. |
| 4,981,977 A | 1/1991 | Southwick et al. |
| 5,011,771 A | 4/1991 | Bellet et al. |
| 5,034,506 A | 7/1991 | Summerton et al. |
| 5,055,556 A | 10/1991 | Stryer et al. |
| 5,082,928 A | 1/1992 | Best |
| 5,084,398 A | 1/1992 | Huston et al. |
| 5,089,419 A | 2/1992 | Kuniyuki |
| 5,132,432 A | 7/1992 | Haugland et al. |
| 5,151,507 A | 9/1992 | Hobbs et al. |
| 5,187,085 A | 2/1993 | Lee |
| 5,187,288 A | 2/1993 | Kang et al. |
| 5,196,306 A | 3/1993 | Bobrow et al. |
| 5,208,148 A | 5/1993 | Haugland et al. |
| 5,227,487 A | 7/1993 | Haugland et al. |
| 5,229,302 A | 7/1993 | Miyazaki et al. |
| 5,242,805 A | 9/1993 | Naleway et al. |
| 5,248,782 A | 9/1993 | Haugland et al. |
| 5,262,658 A | 11/1993 | Jankowski et al. |
| 5,268,486 A | 12/1993 | Waggoner et al. |
| 5,274,113 A | 12/1993 | Kang et al. |
| 5,281,521 A | 1/1994 | Trojanowski et al. |
| 5,292,658 A | 3/1994 | Cormier et al. |
| 5,316,906 A | 5/1994 | Haugland et al. |
| 5,360,895 A | 11/1994 | Hainfeld et al. |
| 5,362,628 A | 11/1994 | Haugland et al. |
| 5,376,557 A | 12/1994 | Schmitt |
| 5,418,155 A | 5/1995 | Cormier et al. |
| 5,433,896 A | 7/1995 | Kang et al. |
| 5,442,045 A | 8/1995 | Haugland et al. |
| 5,443,953 A | 8/1995 | Hansen et al. |
| 5,443,986 A | 8/1995 | Haughland et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,558,991 A | 9/1996 | Trainor |
| 5,561,045 A | 10/1996 | Dorval et al. |
| 5,565,332 A | 10/1996 | Hoogenboom et al. |
| 5,569,587 A | 10/1996 | Waggoner |
| 5,569,766 A | 10/1996 | Waggoner et al. |
| 5,576,424 A | 11/1996 | Mao et al. |
| 5,583,001 A | 12/1996 | Bobrow et al. |
| 5,585,243 A | 12/1996 | Aster et al. |
| 5,602,240 A | 2/1997 | De Mesmaeker et al. |
| 5,627,027 A | 5/1997 | Waggoner |
| 5,630,924 A | 5/1997 | Fuchs et al. |
| 5,635,603 A | 6/1997 | Hansen et al. |
| 5,637,258 A | 6/1997 | Goldburt et al. |
| 5,679,519 A | 10/1997 | Oprandy |
| 5,696,157 A | 12/1997 | Wang et al. |
| 5,731,158 A | 3/1998 | Bobrow et al. |
| 5,736,137 A | 4/1998 | Anderson et al. |
| 5,736,330 A | 4/1998 | Fulton et al. |
| 5,766,941 A | 6/1998 | Cormier et al. |
| 5,773,236 A | 6/1998 | Diwu et al. |
| 5,789,157 A | 8/1998 | Jensen et al. |
| 5,798,276 A | 8/1998 | Haugland et al. |
| 5,798,441 A | 8/1998 | Cormier et al. |
| 5,808,044 A | 9/1998 | Brush et al. |
| 5,830,912 A | 11/1998 | Gee et al. |
| 5,846,737 A | 12/1998 | Kang |
| 5,869,274 A | 2/1999 | Tsao et al. |
| 5,872,221 A | 2/1999 | Martin et al. |
| 5,877,310 A | 3/1999 | Reddington et al. |
| 5,891,741 A | 4/1999 | Siiman et al. |
| 5,948,386 A | 9/1999 | Katti |
| 5,969,135 A | 10/1999 | Ramasamy |
| 5,969,157 A | 10/1999 | Vicenzi |
| 5,981,180 A | 11/1999 | Chandler et al. |
| 5,994,143 A | 11/1999 | Bieniarz et al. |
| 6,002,003 A | 12/1999 | Shen et al. |
| 6,004,536 A | 12/1999 | Leung et al. |
| 6,008,373 A | 12/1999 | Waggoner et al. |
| 6,030,773 A | 2/2000 | Agnello et al. |
| 6,043,025 A | 3/2000 | Minden et al. |
| 6,080,868 A | 6/2000 | Lee et al. |
| 6,114,038 A | 9/2000 | Castro et al. |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,146,836 A | 11/2000 | Barlow |
| 6,150,123 A | 11/2000 | Cosma et al. |
| 6,162,931 A | 12/2000 | Gee et al. |
| 6,166,202 A | 12/2000 | Simmonds et al. |
| 6,179,912 B1 | 1/2001 | Barbera-Guillem et al. |
| 6,214,568 B1 | 4/2001 | Endl et al. |
| 6,221,602 B1 | 4/2001 | Barbera-Guillem et al. |
| 6,229,055 B1 | 5/2001 | Klaubert et al. |
| 6,261,779 B1 | 7/2001 | Barbera-Guillem et al. |
| 6,274,324 B1 | 8/2001 | Davis et al. |
| 6,287,785 B1 | 9/2001 | Shinoki et al. |
| 6,303,755 B1 | 10/2001 | Deo et al. |
| 6,306,610 B1 | 10/2001 | Bawendi et al. |
| 6,326,144 B1 | 12/2001 | Bawendi et al. |
| 6,339,392 B1 | 1/2002 | Ashihara t al. |
| 6,342,588 B1 | 1/2002 | Osbourn |
| 6,348,596 B1 | 2/2002 | Lee et al. |
| 6,352,830 B1 | 3/2002 | Crabtree et al. |
| 6,399,392 B1 | 6/2002 | Haugland et al. |
| 6,475,808 B1 | 11/2002 | Wagner et al. |
| 6,482,655 B1 | 11/2002 | Wei et al. |
| 6,541,618 B1 | 4/2003 | Lee et al. |
| 6,787,638 B1 | 9/2004 | Watkins et al. |
| 6,855,551 B2 | 2/2005 | Bawendi et al. |
| 6,972,326 B2 | 12/2005 | Haugland et al. |
| 6,974,873 B2 | 12/2005 | Leung et al. |
| 6,977,305 B2 | 12/2005 | Leung et al. |
| 2002/0034771 A1 | 3/2002 | Frank et al. |
| 2002/0064794 A1 | 5/2002 | Leung et al. |
| 2002/0077487 A1 | 6/2002 | Leung et al. |
| 2002/0081635 A1 | 6/2002 | Thomas et al. |
| 2002/0094534 A1 | 7/2002 | Greene et al. |
| 2002/0132254 A1 | 9/2002 | Twu et al. |
| 2003/0073149 A1 | 4/2003 | Archer et al. |
| 2007/0269902 A1 | 11/2007 | Beechem et al. |
| 2009/0124511 A1 | 5/2009 | Archer et al. |

FOREIGN PATENT DOCUMENTS

| | | |
|---|---|---|
| EP | 0205198 A1 | 12/1986 |
| EP | 0269451 | 6/1988 |
| EP | 0291086 | 11/1988 |
| EP | 0292810 | 11/1988 |
| EP | 0307754 | 3/1989 |
| EP | 0310132 | 4/1989 |
| EP | 0368674 | 5/1990 |
| EP | 0396505 A2 | 11/1990 |
| EP | 0389301 | 5/1991 |
| EP | 0509718 | 10/1992 |
| EP | 0566205 | 10/1993 |
| EP | 5281521 | 1/1994 |

| | | |
|---|---|---|
| EP | 0599803 | 6/1994 |
| EP | 0629857 | 12/1994 |
| EP | 0794261 | 9/1997 |
| EP | 0918218 | 5/1999 |
| EP | 0989406 | 10/1999 |
| EP | 0603107 | 4/2000 |
| EP | 1054258 | 11/2000 |
| EP | 1442302 | 8/2004 |
| EP | 1065250 | 12/2004 |
| GB | 2302094 | 1/1997 |
| JP | 60082966 | 5/1985 |
| JP | 62174029 | 7/1987 |
| JP | 01-131458 | 5/1989 |
| JP | 02-076600 | 3/1990 |
| JP | 2000310638 | 11/2000 |
| JP | 2001059845 | 3/2001 |
| WO | 8906799 A1 | 7/1989 |
| WO | 8912231 A1 | 12/1989 |
| WO | 9102547 | 5/1991 |
| WO | 9118291 A1 | 11/1991 |
| WO | 97/17610 | 5/1997 |
| WO | 97/40104 | 10/1997 |
| WO | 99/051702 | 10/1999 |
| WO | 9967642 A2 | 12/1999 |
| WO | 01/21624 | 3/2001 |
| WO | 02/26891 | 4/2002 |
| WO | 03/030817 | 4/2003 |

OTHER PUBLICATIONS

"Fab Fragment Monovalent Antibodies", *Rockland Immunochemicals for Research Product Litrature*, printed Sep. 30, 2002.
"Nanogold-Antibody Conjugates", updated Nov. 20, 2001.
10181177.6, European Search Report mailed on Feb. 3, 2011.
EP02768949, European Search Report mailed Feb. 23, 2007.
EP02768949, Extended European Search Report mailed Jan. 15, 2010.
EP02768949, Supplemental European Search Report mailed Feb. 28, 2007.
EP09163588, European Search report mailed on Jan. 15, 2010.
PCT/US02/31416, International Preliminary Report on Patentability mailed Aug. 26, 2003.
PCT/US02/31416, International Search Report mailed Jul. 16, 2003.
Andrew, Sarah M. et al., "Fragmentation of Immunoglobulin", *Current Protocols in Cell Biology*, 2000, 16.4.1-16.4.10.
Attiya, Said et al., ""Affinity protection chromatography for efficient labeling of antibodies for use in affinity capillary electrophoresis"", *Electrophoresis*, 23, 2002, 750-758.
Bacigalupo, M. A. et al., ""Analytical performance of luminescent immunoassays of different format for serum daidzein analysis"", *Fresenius J. Anal Chem.*, 370 , 2001, 82-87.
Barbara, et al., ""A simple indirect ELISA using F(ab')2 fragments of immunoglobulin"", *J. Gen. Virol.*, 58, 1982, 315-322.
Beisker, Wolfgang et al., "An Improved Immunocytochemical Procedure for High-Sensitivity Detection of Incorporated Bromodeoxy", *Cytometry*, 8, 1987, 235-239.
Beverloo, et al., "Immunochemical detection of proteins and nucleic acids on filters using small luminescent inorganic crystals as marker.", *Analytical Biochemistry*, 203, 1992, 326-34.
Bird, et al., "Single-chain antigen-binding proteins", *Science*, 242, 1988, 423-426.
Bjorck, Lars et al., "Purification and Some Properties of *Streptococcal* Protein G, A Novel IgG-Binding Reagent", *The Journal of Immunology*, 133(2), 1984, 969-974.
Boenisch, Thomas, "Formalin-Gixed and Heat-Retrieved Tissue Antigens: A comparison of their immunoreactivity in experimental antibody diluents", *J. Molecular Morphology*, 9(2), 2001, 176-179.
Brelje, T. C. et al., ""Multicolor Laser scanning confocal immunofluorescence microscopy: practical application and limitations"", *Methods Cell Biol* 38:, 1993, 97-181.
Brinkley, Michael, "A Brief Survey of Methods for Preparing Protein Conjugates with Dyes, Haptens, and Cross-Linking Reagents", *Bioconjugate Chemistry*, vol. 3, Issue 1, 1992, pp. 2-13.

Brown, Jeremy K. et al., "Primary Antibody- Fab Fragment Alternative to Traditional Direct and Indirect Immunolabeling Techniques", *Journal of Histochemistry & Cytochemistry*, vol. 52, No. 9, 2004, 1219-1230
Butler, J E. et al., "Amplification of the Enzyme-Linked Immunosorbent Assay (ELISA) in the Detection of Class-SPecific Antibodies ", *Journal of Immunological Methods*, vol. 20, Apr. 1978, 365-383.
Camera, Luigi et al., "Evaluation of the Serum Stability and In Vivo Biodistribution of CHX-DTPA and Other Ligands for Yttrium Labeling of Monoclonal Antibodies", *J. Nul. Med.*, 35, 1994, 882-889.
Capo, C. et al., ""Dimethylsulphoxide induction of murine macrophage-like line P388D1: change of phagocytic ability and cell surface properties"", *J Cell Sci.* 64:, 1983, 281-93.
Chase, G. D., "Medical Applications of Radioisotopes", *Remmington's Pharmaceutical Sciences*, 18th Edition , 1990, 624-52.
Chemicon International, "Product Literature", *Product Literature*, May 29, 2001.
Clancy, B. et al., "Reduction of Background Autofluorescence in Brain Sections Following Immersion in Sodium Borohydride", *Journal of Neuroscience Methods*, 83, 1998, 97-102.
Cooper, Helen M. et al., "Production of Antibodies", *Current Protocols in Immunology*, 1995, 2.4.1-2.4.9 .
Coulter, et al., "Simplified preparation of rabbit Fab fragments", *Journal of Immunological Methds*, vol. 59, 1983, 199-203.
Davidson-Moncada, J K. et al., "Involvement of protein kinase D in Fc gamma-receptor activation of the NADPH oxidase in neutrophils", *Biochem J*, 363:1, 2002, 95-103.
De Bellefontaine, et al., "Immunoassay for native enzyme quantification in biological samples", *Applied Biochemistry and Biotechnology*, vol. 48, 1994, 117-123.
Delespesse, et al., "Radioimmunoassay for human antihyroglobulin antibodies of different immunoglobulin classes", *Horm. Metab. Res.*, 8, 1976, 50-54.
Dos Remedios, Cristobal G. et al., "Fluorescence Resonance Energy Transfer Spectroscopy is a Reliable "Ruler" for Measuring Structural Changes in Proteins", *Journal of Structural Biology*, vol. 115, 1995, pp. 175-185.
Dudich, et al., "Polarization fluorescence, spin label and ultracentrifugal studies of specific interaction of low molecular weight proteins with the fc fragment of human immunoglobulin G", *Molecular Immunology*, 20, 1983, 1267-1272.
Eichmuller, Stefan et al., "A New Method for Double Immunolabelling with Primary Antibodies from Identical Species", *Journal of Immunological Methods*, vol. 190, No. 2, Elsevier Science Pubishers, B.V. Amsterdam, NL., Apr. 19, 1996, 255-265.
Eliasson, Margareta et al., "Chimeric IgG-binding Receptors Engineered from *Straphylococcal* Protein A and *Streprtococcal* Protein G", *American Society of Biochemistry and Molecular Biology*, Aug. 27, 1987, 4323-4327.
Eliasson, Margareta et al., "Differential IgG-Binding Characteristics of *Staphylococcal* Protein G, and a Chimeric Protein AG", *The Journal of Immunology*, 142, 1989, 575-581.
Ferri, Gian-Luca et al., "Quadruple Immunofluorescence: A Direct Visualization method", *Journal of Histochemistry and Cytochemistry*, vol. 45, No. 2, 1997, 155-158.
Fraker, Pamela J. et al., "Protein and Cell Membrane Iodinations with a Sparingly Soluble Chloroamide 1,3,4,6-tetraciloro-3a, 6a-Diphenyglcoluril", *Biochemical and Biophysical Research Comm.*, 80(4), 1978, 849-857.
Friedman, et al., "Sensitive solid-phase radioimmunoassay for detection of human immunoglobulin G antibodies to *varicella-zoster* virus", *Journal of Clinical Microbiology*, 9, 1979, 1-10.
Friedman, M.G., "A population Screening test for antibody to measles virus", *Isr J Med Sci* 17 (11), 1981, 1045-50.
Gandhi, et al., "Enzyme linked protein-A: an ELISA for detection of amoebic antibody", *Transactions of the Royal Society of Tropical Medicine and Hygiene*, 81, vol. 81, No. 2, Jan. 2, 1987, 183-185.
Gandhi, B. M. et al., "Enzyme linked protein—A: an ELISA for detection of IgG antibodies against Mycobacterium tuberculosis in intestinal tuberculosis", *Tubercle*, vol. 67, 1986, 219-224.

Gennaro, et al., "Medical application of Radioisotops", in Remmington's Pharmaceutical Sciences, 18th Edition., Mack Publishing Co., 624, 1990.
Gibbons, et al., "Enzyme-enhancement immunoassay: a homogeneous assay for polyvalent ligands and antibodies", Clin. Chem. 27, 1981, 1602-1608.
Goding, James W., "Use of Staphylococcal Protein A As An Immunological Reagent", Journal of Immunological Methods, vol. 20, Apr. 1978, 241-258.
Gonatas, N K. et al., "Ultrastructural Autoradiographic Detection of Intracellular Immunoglobulins With Iodinated Fab Fragments of Antibody. The Combined use of Ultrastructural Autoradiography and Peroxidase Cytochemistry for the Detection of Two Antigens (Double Labeling)", Journal of Histochemistry and Cytochemistry, vol. 22, No. 11., Database Embase, Database Accession No. EMB—1975166176, Abstract, 1974, 999-1009.
Gorevic, Peter D. et al., "Immunoglobulin G (IgG)", Methods in Enzymology, vol. 116, 1985, 3-25.
Goroff, et al., "Activation of B cells in vivo by a Fab/Fc fragment of a monoclonal anti-IgD antibody requires an interaction between the antibody fragment and a cellular IgG Fc receptor", Journal of Immunology, 140, 1988, 2919-2924.
Haab, Brian B. et al., "Protein microarrays for highly parallel detection and quantitation of specific proteins and antibodies in complex solutions", Genome Biology, vol. 2, No. 2, 2001, 1-13.
Hanly, W. C. et al., "Review of Polyclonal Antibody Production Procedures in Mammals and Poultry", ILAR Journal, vol. 37, No. 3, 1995, 93-117.
Hansen, et al., "Enzyme-linked immunosorbent assay (ELISA) for direct quantifcation of surface-bound platelet immunogloblins", Scand. J. Clin. Lab. Invest, vol. 43, 1984, 513-519.
Hanson, Bonnie J. et al., "A Novel subfractionation approach for mitochondrial proteins: A three-dimensional mitochondrial proteome map", Electrophoresis, 22, 2001, 950-959.
Harris, T N. et al., "A preparation of Fc fragment of normal mouse IgG1 for production of rabbit anti mouse IgG1 serum", Journal of Immunological Methods, vol. 8, No. 3, Sep. 1975, 203- 212.
Haugland, Richard P., "Handbook of Fluorescent Probes and Research Products", Ch 1-3.3, Molecular Probes, Inc/Invitrogen, 2002, 2002, 11-118.
Haugland, Richard P., "Molecular Probes Handbook of Fluorescent Probes and Research Chemicals", Ch 22: Indicators for Ca2+, Mg2+, Zn2+, and Other Metals, Sixth Edition and its subsequent 7th edition and 8th edition updates issued on CD ROM in Nov. 1999 and May 2001, Molecular Probes, Inc., 1996, 503-544.
Haugland, Rosario P., "Antibody Conjugates for Cell Biology", Current Protocols in Cell Biology, 2000, 16.5.1-16.5.22.
Haugland, Rosaria P. et al., "Coupling of monoclonal antibodies with biotin", Methods in Molecular Biology, vol. 45, 1995, 223-233.
Haugland, Rosaria P. et al., "Coupling of monoclonal antibodies with enzymes", Methods in Molecular Biology, vol. 45, 1995, 235-243.
Haugland, Rosaria P., "Coupling of monoclonal antibodies with fluorophores", Methods in Molecular Biology, Monoclonal Antibody Protocols, vol. 45, 1995, pp. 205-243.
Hsu, et al., "A comparision of ABC, unlabeled antibody and conjugated immunohistochemical methods with monoclonal and polyclonal antibodies—an examination of germinal center of tonsils", American Society of Clinical Pathologists, 80, 1983, 429-435.
Hsu, et al., "The use of antiavidin antibody and avidin-biotin peroxidase complex in immunoperoxidase technique", AMerican Society of Clinical Pathologists, 75, 1981, 816-821.
Hsu, S.M. et al., "Protein A, avidin and biotin in immunohistochemistry", The Journal of Histochemistry & Cytochemistry, 18, 1981, 1349-1353.
Huston, et al., "Protein engineering of antibody binding sites: Recovery of specific activity in an anti-digoxin single-chain Fv analogue produced in Escherichiacoli", Proceedings of the National Academy of Sciences (PNAS), 85(16), 1988, 5879-5883.
Ino, Hidetoshi, "Application of Antigen Retrieval by Heating for Double-label Fluorescent Immunohistochemistry with Identical Species-derived Pimary Antibodies", Journal of Histochemistry & Cytochemistry, 2004, 1209-1217.

Kachidian, P. et al., "Dual Immunocytochemistry Using Iodine-125-Labeled Protein A A new Electron Microscopic Technique Applied to the Investigation of Chemical Connectivity and Axonal Tansmitter Co-Localization in the Brain", Journal of Neuroscience Methods, vol. 38, No. 2-3, 1991, 115-128.
Kaplan, et al., "A radiolabeled staphylococcal protein A assay for detection of anti-erythrocyte IgG in warm agglutinin autoimmune hemolytic anemia of dogs and man", Veterinary Immunology and Immunopathology, vol. 4, 1983, 307-317.
Kariwa, et al., ""Development and application of protein G antibody assay for the detection of antibody to hantavirus"", Journal of Virological Methods 37. 1992, 345-354.
Kato, Kanefusa et al., "Coupling Fab fragment of rabbit anti-human IgG antibody to beta-D-galactosidase and a highly sensitive immunoassay of human IgG", Febs Letters, vol. 56, No. 2, Aug. 1975, 370-2.
Kato, Kanefusa et al., "Enzyme-linked immunoassay.ll. A simple method for synthesis of rabbit antibody-beta-D-galactosidase complex and its general applicability", Journal of Biochemistry, vol. 78, 1975, 423-425.
Kato, Kanefusa et al., "Enzyme-linked immunoassay: conjugation of the Fab' fragment of rabbit IgG with beta-D-galactosidase from E. coli and its use for immunoassay", The Journal of Immunology, vol. 116, No. 6, Jun. 1976, 1554-1560.
Kho, R. et al., "Zinc-histidine as nucleation centers for growth of ZnS nanocrystals", Biochemical and Biophysical Research Communications, vol. 272, No. 1, 2000, 29-35.
Kimura, S. et al., "High galactosylation of oligosaccharide in umbilical cord blood IgG, and its relationship to placental function", Clin Chim Acta, 299 (1-2), 2000, 169-77.
Koksch, Mario et al., "Fluorescence resonance energy transfer as a new method for the epitope-specific characterization of anti-platelet antibodies", Journal of Immunological Methods, vol. 187, No. 1, Nov. 16, 1995, 53-67.
Kricka, L. J. et al., "Detection of Energy Transfer and Fluorescence Quenching", Nonisotopic DNA Probe Techniques, San Diego: Academic Press, Inc., 1992, 311-353.
Kruger, N J., "Detection of Polypeptides on Immunoblots Using Secondary Antibodies or Protein A", Methods in Molecular Biology (Clifton, N.J.), vol. 32, 1994, 215-226.
Lagoo, et al., ""Early activation and cell cycle entry of resting B cells after Fab-anti-Ig treatment: role of receptor crosslinking"", Cellular Immunology, 118, 1989, 53-67.
Lamoyi, Edmundo , "Preparation of F(ab')2 Fragments from Mouse IgG of Various Subclasses", Methods in Enzymology 121, 1986, 652-663.
Langone, "Protein Aof Staphylococcus aureus and related immunoglobin receptors produced by streptococci and pneumonococci", Adv. Immunol. 32, 1982, 157-252.
Lindgren, A et al., "Optimisation of a heterogeneous non-competitive flow immunoassay comparing fluorescein, peroxidase and alkaline phosphatase as labels", Journal of Immunological Methods, vol. 211, 1998, 33-42.
Lu, Qi L. et al., "A new blocking method for application of murine monoclonal antibody to mouse tissues sections", The Journal of Histochemistry & Cytochemistry, vol. 46, No. 8, 1998, 977-983.
Lydyard, et al., "The antibody repertoire of early human B cells. I. High frequency of autoreactivity and polyreactivity ", Scand. J. Immunol. 31, 1990, 33-43.
March, et al., "The specificity of human autoantibodies to IgG: the development of methodology for measuring the specificity of antiglobulin isotypes in rheumatoid and normal sera", Rheumatology, 6, 1986, 155-160.
Marshall, L. et al., "Antenatal platelet antibody testing by flow cytometry—result of a pilot study", Transfusion, vol. 34, No. 11, 1994, 961-965.
Matayoshi, et al., "Novel Fluoregenic Substrates for Assaying Retroviral Proteases by Resonance Energy Transfer", Science, vol. 247, Feb. 23, 1990, pp. 954-958.
Muratsugu, et al., "Plasma-polymerized allylamine film used as a new solid phase in immunoradiometric assay (IRMA): effect of antibody (F(ab')2 fragment) concentration on dose response in two-site IRMA", Chem. Pharm. Bul., 40, 1992, 501-503.

Myung Ja, "Application Serial No. PCT/01/30404", Choi, Joong Ho, May 3, 2001.

Nanoprobes, "Nanoprobes Fab-3 Gold-Antibody Conjugates", printed Sep. 30, 2002.

Nanoprobes, "Nanoprobes Gold-Antibody Conjugates", Mar. 2000.

Naot, et al., "Methods for avoiding false-positive results occuring in immunoglobulin M enzyme-linked immunosorbent assays due to presence of both rheumatoid factor and antinuclear antibodies", *Journal of clinical Microbiology*, vol. 14, No. 1, 1981, 73-78.

Negoescu, Adrien et al., "F(ab) Secondary Antibodies: A General Method for Double Immunolabeling With Primary Antisera From the Same Species. Effciency Control by Chemiluminescence", *Journal of Histochemistry and Cytochemistry*, vol. 42, No. 3, 1994, 433-437.

Neuweiler, H. et al., "Detection of individual p53-autoantibodies by using quenched peptide-based molecular probes", *Angewandte Chemie International Edition in English*, vol. 41 No. 24, 2002, 4769-73.

Nitta, Taizo et al., "Bispecific F (ab')2 monomer prepared with anti-CD3 and anti-tumor monoclonal antibodies is most potent in induction of cytolysis of human T cells", *Eur. J. Immunol.* 19, 1989, 1437-1441.

Notani, Gursarab W. et al., "Versatility of *Staphylococcus aureur* Protein A in Immunocytochemistry", *Journal of Histochemistry and Cytochemistry*, 27, 1979, 1438-1444.

Owens, Raymond J. et al., "The genetic engineering of monoclonal antibodies", *Journal of Immunological Methods*, vol. 168, No. 2, 1994, 149-165.

Pezzuto, et al., "Clinical Use of Monoclonal Antibodies", *In Biotechnology and Pharmacy*, Chapman & Hall 227, 1993, 227-249.

Poglitsch, Claudia L. et al., "Interaction of Antibodies with Fc Receptors in Substrate-Supported Planar Membranes Measured by Total Internal Reflection Fluorescence Microscopy", *Biochemistry*, 29, 1990, 248-254.

Ponder, "Cell Marking Techniques and their application", *Mammalian Development: A Practical Approach*, Monk (ed.), 1987, 115.

Pope, et al., "IgG rheumatoid factor: analysis of various species of IgG for detection by radioimmunoassay", *J. Lab. Clin. Med.*, 97, 1981, 842-853.

Reif, Oscar-Werner et al., "Fluorescein isothiocyanate-labeled protein G as an affinity ligand in affinity/immunocapillary electrophoresis with fluorescence detection", *Analytical Chemistry*, vol. 66, No. 22, Nov. 1994, 4027-4033.

Remmington, "Remmington's Pharmaceutical Sciences", 18th Ed., 1990.

Rubenstein, et al., "Homogeneous enzyme immunoassay. A new immunochemical technique", *Biochemical & Biophysical Research Communication*, vol. 47, 1972, 846-851.

Saltzman, W. M. et al., "Transport rates of proteins in porous materials with known microgeometry", *Biophys. J.*, 55, 1989, 163-171.

Schena, M. et al., "Microarray Biochip Technology", *Chapters 1 and 2, Eaton Publishing*, MA., U.S. Appl. No. 6714299, 2000, 1-38.

Selvin, Paul R., "Fluorescence Resonance Energy Transfer", *Methods in Enzymology*, vol. 246, 1995, 300-334.

Shea, Michael et al., "High-performance liquid chromatographic measurement of exogenous thiosulfate in urine and plasma", *Analytical Biochemistry*, vol. 140, No. 2, Aug. 1, 1984, 589-594.

Sheikh, Sohail H. et al., "Development of a Fluorescence Immunoassay for Measurement of Paclitaxel in Human Plasma", *Analytical Biochemistry*, vol. 283, Jul. 15, 2000, 33-38.

Sherwood, Jill K. et al., "Controlled Antibody Delivery Systems", *Biotechnology*, 10, 1992, 1446-9.

Shi, et al., "Antigen Retrieval Immunohistochemistry Under the Influence of pH Using Monolonal Anibodies", *The Journal of Histochemistry & Cytochemistry*, vol. 43, No. 2, Feb. 1995, 193-201.

Shi, S. R. et al. "Antigen retrieval immunohistochemistry: past, present, and future", J. Histochem Cytochem, vol. 43, No. 3, 1997, 327-43.

Shi, S. R. et al., "Antigen retrieval immunohistochemistry and molecular morphology in the year 2001", *Appl. Immunohistochem. Molecul. Morphol.*, 9(2), 2001, 107-16.

Shi, S. R., "Antigen retrieval in formalin-fixed, paraffin-embedded tissues: and enhancement method for immunohistochemical staining based on microwave oven heating of tissue sections", J. Histochem Cytochem, vol. 39, No. 6, 1991, 741-748.

Silver, Anne et al., "Immunoassays for low concentrations of albumin in urine", *Clinical Chemistry*, vol. 32, No. 7, 1986, 1303-1306.

Singh, et al., "A direct binding assay for rheumatoid factor serum antiglobulins using fluorescein-labelled Fc fragment of human immunoglobulin-G", *Journal of Clinical Pathology*, vol. 31, 1978, 963-973.

Sisson, Thomas H. et al., "An improved method for immobilizing IgG antibodies on protein A-agarose", *Journal of Immunological Methods*, vol. 127, No. 2, Mar. 9, 1990, 215-220.

Slu, Shan-Rong et al., "Antigen Retrieval Immunohistochemistry: Past, Present, and Future", J. histochem. cytochem., 45, 1997, 327-343.

Springer, et al., "Monoclonal antibodies specific for rat IgG1", *Hybridoma*, vol. 1, No. 3, 1982, 257-273.

Sternberger, Ludwig A. et al., "The unlabeled antibody enzyme method of immunohistochemistry: preparation and properties of soluble antigen-antibody complex (horseadish peroxidase-antihorseadish peroxidase) and its use in identification of spirochetes", *The Journal of Histochemistry & Cytochemistry*, 18, 1970, 315-333.

Stirling, John W., "Immuno- and Affinity Probes for Electron Microscopy: A Review of Labelling and Preparation Techniques", *Journal of Hitohemicstryf Cytochemistry*, vol. 38, No. 2, 19992, 145-15.

Sun, Shuhua et al. "Chimareic Protein A/protein G and Protein g/alkaline phosphatase as reporter molecules", *Journal of Immunological Methods*, vol. 152, No. 1, Jul. 31, 1992, 43-48.

Suola, Avadhesha et al., "Protein A: Nature's Universal Anti-body", *TIBS*, Feb. 1982, 74-76.

Tagliaferro, P. C. et al., "Immunofluorescence and glutaraldehyde fixation. A new procedure based on Schiff-quenching method", *Journal of Neuroscience Methods*, 77, 1997, 191-197.

Tarkowski, Andrej et al., "False positive results in class-specific rheumatoid factor (RF) assays due to interaction between RF and FC fragments of anti-immunoglobulin indicator reagents", *Journal of Immunological Methods*, vol. 58, No. 1-2, Mar. 1983, 171-182.

Tarkowski, Andrej et al., "Solid-phase enzyme-linked immunospot (ELISPOT) assay for enumeration of IgG rheumatoid factor-secreting cells", *Journal of Immunological Methods*, vol. 72, No. 2, Sep. 4, 1984, 451-459.

Togawa, T. et al., "High performance liquid chromatographic determination of bound sulfide and sulfite and thiosulfate at their low levels in human serum by pre-column fluorescence derivatization with monobromobimane", *Chem pharm Bull (Tokyo) 40(11):*, 1992, 3000-4.

Tyagi, et al., "Molecular Beacons: Probes that Fluoresce upon Hybridization", *Nature Biotechnology*, vol. 14, No. 3, Mar. 1996, 303-308.

Tyagi, Sanjay et al., "Multicolor molecular beacons for allele discrimination", *Nature Biotechnology*, vol. 16, 1998, 49-53.

Ullman, et al., "Fluoresnce excitation transfer immunoassay (FETI)", *Methods in Enzymology*, 74, 1981, 28-60.

Ullman, E. F. et al., "Fluorescent excitation transfer immunoassay. A general method for determination of antigens", *J Biol Chem Int Ed Engl 41(24)*, 1976, 4172-8.

Van Der Loos, Chris M. et al., "The Animal Research Kit (ARK) can be Used in a Multistep Double Staining Method for Human Tissuew Specimens", *Journal of Histochemistry and Cytochemistry*, vol. 48, No. 10, 2000, 1431-1437.

Ward, et al., "Binding activities of a repertoire of single immunoglobulin variable domains secreted from *Escherichia coli*", *Nature*, 341, 1989, 544-546.

Wei, A. P. et al., "Antibody-mediated fluorescence enhancement based on shifting the intramolecular dimer<—>monomer equilibrium of fluorescent dyes", *Anal Chem 66(9)*, 1994, 1500-6.

Wei, A. P. et al., "Bifluorophoric molecules as fluorescent beacons for antibody-antigen binding", *J Mol Recognit 15(5)*, 2002, 311-20.

Wessel, Gary M. et al., "Two Embryonic, Tissue-Specific Molecules Identified by a Double-Label Immunofluorescence Technique for Monoclonal Antibodies", *Journal of Histochemistry and Cytochemistry*, vol. 34, No. 6, 1986, 703-706.

Wu, Pengguang et al., "Resonance Energy Transfer: Methods and Applications", *Analytical Biochemistry*, vol. 218, No. 1, 1994, 1-13.

Zhang, Ji-Hu et al., "A Simple Statistical Parameter for Use in Evaluation and Validation of High Throughput Screening Assays", *Journal of Biomolecular Screening*, vol. 4, No. 2, 1999, 67-73.

Zhang, Ke et al., "A secreted mucin carrying sialyl-Lewis a from colon carcinoma cells binds to E-selectin and inhibits HL-60 cell adhesion", *International Journal of Cancer*, vol. 59, No. 6, 1994, 823-9.

Zhang, Y-Z. et al., "Cell fusion Monitored with Long-Term Cell Tracking, Fluorescent Probes", Molecular Biology of the Cell, vol. 3, Abstract# 525, Nov. 1992, 90a.

Zuk, et al., "Fluorescence protection immunoassay: a new homogeneous assay technique", *Clin. Chem. 25*, 1979, 1554-1560.

\* cited by examiner

ANTIBODY COMPLEXES AND METHODS FOR IMMUNOLABELING

CROSS-REFERENCE TO RELATED APPLICATIONS

This application is a division of U.S. application Ser. No. 12/047,131 filed Mar. 12, 2008, which is a continuation of U.S. application Ser. No. 10/467,550 filed Oct. 12, 2004 (now abandoned), which is a 371 national stage of International application No. PCT/US02/31416 filed Oct. 2, 2002, which is a continuation of U.S. application Ser. No. 10/118,204 filed Apr. 5, 2002, which claims priority to U.S. application Ser. No. 60/369,418 filed Apr. 1, 2002, and 60/329,068 filed Oct. 12, 2001, which disclosures are herein incorporated by reference in their entirety.

FIELD OF THE INVENTION

The present invention relates to immuno-labeled complexes and methods for use in the detection and measurement of one or more targets in a biological sample. The invention has applications in the fields of molecular biology, cell biology, immunohistochemistry, diagnostics, and therapeutics.

BACKGROUND OF THE INVENTION

Immunolabeling is a method for qualitative or quantitative determination of the presence of a target in a sample, wherein antibodies are utilized for their specific binding capacity. The antibodies form a complex with the target (antigen), wherein a detectable label is present on the antibody or on a secondary antibody. The detectable label is a key feature of immunolabeling, which can be detected directly or indirectly. The label provides a measurable signal by which the binding reaction is monitored providing a qualitative and/or quantitative measure of the degree of binding. The relative quantity and location of signal generated by the labeled antibodies can serve to indicate the location and/or concentration of the target. The label can also be used to select and isolate labeled targets, such as by flow sorting or using magnetic separation media. Examples of labels include but are not limited to radioactive nucleotides ($^{125}I$, $^3H$, $^{14}C$, $^{32}P$), chemiluminescent, fluorescent, or phosphorescent compounds (e.g., dioxetanes, xanthene, or carbocyanine dyes, lanthanide chelates), particles (e.g., gold clusters, colloidal gold, microspheres, quantum dots), and enzymes (e.g., peroxidases, glycosidases, phosphatases, kinases). Ideally, the label is attached to the antibody in a manner that does not perturb the antibody's binding characteristics but enables the label to be measured by an appropriate detection technology. The choice of labels is influenced by factors such as ease and sensitivity of detection, equipment availability, background in the sample (including other labels) and the degree to which such labels are readily attached to the particular antibody. Both direct and indirect labeling of antibodies is utilized for immunolabeling. Direct labeling utilizes only a primary antibody, i.e. the antibody specific for the target, bound to the label. In contrast, indirect labeling utilizes a secondary antibody bound to the label, which is specific for the primary antibody, e.g. a goat anti-rabbit antibody. The principal differences in immunolabeling methods and materials reside in the way that the label is attached to the antibody-antigen complex, the type of label that is used, and the means by which the antibody-antigen complex is detected.

Limitations for direct labeling primary antibodies include the need for buffers free of primary amines, or carrier proteins such as bovine serum albumin (BSA), and other compounds such as tris-(hydroxymethyl)aminomethane (TRIS), glycine, and ammonium ions. These materials are, however, common components in antibody buffers and purification methods, and it may not be possible or feasible to remove them prior to the coupling reaction. In particular, many monoclonal antibodies are available only as ascites fluid or in hybridoma culture supernatants, or diluted with carrier proteins, such as albumins. Thus, direct labeling of antibodies in ascites fluid or other medias containing interfering compounds is not attainable.

The indirect immunolabeling method typically involves a multi-step process in which an unlabeled first antibody (typically a primary antibody) is directly added to the sample to form a complex with the antigen in the sample. Subsequently, a labeled secondary antibody, specific for the primary antibody, is added to the sample, where it attaches noncovalently to the primary antibody-antigen complex. Alternatively, a detectable label is covalently attached to an immunoglobulin-binding protein such as protein A and protein G to detect the antibody-antigen complex that has previously been formed with the target in the sample. Using ligands, such as streptavidin, that are meant to amplify the detectable signal also expands this cascade binding.

Indirect immunolabeling often results in false positives and high background. This is due to the fact that secondary antibodies, even when purified by adsorption against related species, nevertheless can exhibit significant residual cross-reactivity when used in the same sample. For example, when mouse tissue is probed with a mouse monoclonal antibody, the secondary antibody must necessarily be a labeled anti-mouse antibody. This anti-mouse antibody will detect the antibody of interest but will inevitably and additionally detect irrelevant, endogenous mouse immunoglobulins inherent in mouse tissue. This causes a significant background problem, especially in diseased tissues, which reduces the usefulness and sensitivity of the assay. Thus, the simultaneous detection of more than one primary antibody in a sample without this significant background interference depends on the availability of secondary antibodies that 1) do not cross-react with proteins intrinsic to the sample being examined, 2) recognize only one of the primary antibodies, and 3) do not recognize each other (Brelje, et al., METHODS IN CELL BIOLOGY 38, 97-181, especially 111-118 (1993)).

To address the background problem in indirect labeling, a number of strategies have been developed to block access of the anti-mouse secondary antibodies to the endogenous mouse immunoglobulins. One such strategy for blocking involves complexing the primary antibody with a selected biotinylated secondary antibody to produce a complex of the primary and secondary antibodies, which is then mixed with diluted normal murine serum (Trojanowski et al., U.S. Pat. No. 5,281,521 (1994)). This method is limited by the necessity to utilize an appropriate ratio of primary-secondary complex. Too low a ratio of primary-secondary complex will cause a decrease in specific staining and increased background levels due to the uncomplexed secondary anti-mouse antibody binding to endogenous mouse antibodies. However, the ability of a whole IgG antibody (as was used in the referenced method) to simultaneously bind and cross-link two antigens results in too high a ratio, causing the complex to precipitate or form complexes that are too large to penetrate into the cell or tissue.

Another strategy for blocking access to endogenous immunoglobulins in the sample involves pre-incubating the sample with a monovalent antibody, such as Fab' fragments, from an irrelevant species that recognize endogenous immunoglobulins. This approach requires large quantities of expensive Fab' fragments and gives mixed results and adds at least two steps (block and wash) to the overall staining procedure. The addition of a cross-linking reagent has resulted in improved reduction of background levels (Tsao, et al., U.S. Pat. No. 5,869, 274 (1997)) but this is problematic when used with fluorophore-labeled antibodies. The cross-linking causes an increase in the levels of autofluorescence and thus the background (J. Neurosci. Meth. 83, 97 (1998); Mosiman et al., Methods 77, 191 (1997); Commun. Clin. Cytometry 30, 151 (1997); Beisker et al., Cytometry 8, 235 (1987)). In addition, pre-incubation with a cross-linking reagent often masks or prevents the antibody from binding to its antigen (J. Histochem. Cytochem. 45, 327 (1997); J. Histochem. Cytochem. 39, 741 (1991); J. Histochem. Cytochem. 43, 193 (1995); Appl. Immunohistochem. Molecul. Morphol. 9, 176 (2001)).

In a variation of this blocking strategy, a multi-step sequential-labeling procedure is used to overcome the problems of cross-reactivity. The sample is incubated with a first antibody to form a complex with the first antigen, followed by incubation of the sample with a fluorophore-labeled goat Fab anti-mouse IgG to label the first antibody and block it from subsequently complexing when the second antibody is added. In the third step, a second mouse antibody forms a complex with the second antigen. Because the second antibody is blocked from cross-reacting with the first antibody, the second mouse antibody is detected with a standard indirect-labeling method using a goat anti-mouse antibody conjugated to a different fluorescent dye (J. Histochem. Cytochem. 34, 703 (1986)). This process requires multiple incubation steps and washing steps and it still cannot be used with mouse antibodies to probe mouse tissue.

Another blocking method is disclosed in the animal research kit (ARK) developed by DAKO. In this kit, a primary antibody is complexed with biotin-labeled goat Fab anti-mouse IgG and excess free Fab is blocked with normal mouse serum. However, since the Fab used in this process is generated from the intact IgG (rather than a selected region) there is a potential for the formation of anti-paratope or anti-idiotype antibodies that will block the antigen-binding site and prevent immunolabeling. The biotinylated antibody also requires subsequent addition of a labeled avidin or streptavidin conjugate for its subsequent visualization.

The present invention is advantageous over previously described methods and compositions in that it provides the benefits of indirect labeling with the easy and flexibility of direct labeling for determination of a desired target in a biological sample. The present invention provides labeled monovalent proteins specific for a target-binding antibody, which are complexed prior to addition with a biological sample. Because these monovalent proteins are not bivalent antibodies, precipitation and cross-linking are not a problem. Therefore the compositions of the present invention can be used with immunologically similar monoclonal or polyclonal antibodies of either an identical isotype or different isotypes. The monovalent labeling reagents are specific for the Fc region of target-binding antibodies, these reagents will not interfere with the binding region of the primary antibody. In addition, the monovalent labeling proteins are not negatively affected by the presence of primary amines like BSA, gelatin, hybridoma culture supernatants or ascites fluid, thus primary antibodies present in these media can be effectively labeled with the labeling reagents of the present invention. Thus, the present invention provides numerous advantages over the conventional methods of immunolabeling.

SUMMARY OF THE INVENTION

The present invention provides labeling reagents and methods for labeling primary antibodies and for detecting a target in a sample using an immuno-labeled complex that comprises a target-binding antibody and one or more labeling reagents. The labeling reagents comprise monovalent antibody fragments or non-antibody monomeric proteins whereby the labeling proteins have affinity for a specific region of the target-binding antibody and are covalently attached to a label. Typically, the labeling reagent is an anti-Fc Fab or Fab' fragment that was generated by immunizing a goat or rabbit with the Fc fragment of an antibody.

The methods for labeling a target-binding antibody with a labeling reagent comprise a) contacting a solution of target-binding antibodies with a labeling reagent, b) incubating said target-binding antibodies and said labeling reagent wherein a region of said target binding antibody is selectively bound by labeling reagent, and c) optionally removing unbound labeling reagent by adding a capture reagent comprising immunoglobulin proteins or fragments thereof that are optionally immobilized on a matrix. The labeling of the target-binding antibody can be performed irrespective of the solution that the antibody is present in and includes proteins that are normally present in serum or ascites. This feature of the labeling process of the target-binding antibody eliminates the need to purify and concentrate the target-binding antibody. The time required for the labeling reagent to selectively bind to the target-binding antibody is typically very short, often less than 10 minutes. Often the labeling reagent binds the target-binding antibody in the amount of time it takes to add and mix the labeling reagent with the target-binding antibody. This formation of an immuno-labeled complex—a target-binding antibody and a labeling reagent—results in the formation of an target detection solution that is used to detect a target in a sample.

The labeling steps of the target-binding antibody are optionally repeated to form a panel of subsets, these immuno-labeled complex subsets may be used individually or pooled wherein each subset is distinguished from another subset by i) the target-binding antibody, or ii) a ratio of label to labeling reagent, or iii) a ratio of labeling reagent to the target-binding antibody or iv) by a physical property of the label. Thus, it is appreciated that a wide range of subsets can be formed wherein the subsets can be used individually to detect a target in a sample or pooled to simultaneously detect multiple targets in a sample. The simultaneous detection of multiple targets in a sample is especially useful in methods that utilize flow cytometry or methods that immobilize a population of cells or tissue on a surface.

The methods for determining a target in a sample using immuno-labeled subsets comprises forming a subset of immuno-labeled complexes, as described above, contacting a sample with said immuno-labeled complexes, incubating the sample for a time sufficient to allow the immuno-labeled complex to selectively bind to a desired target, and illuminating the immuno-labeled complex whereby the target is detected. The sample is any material that may contain a target and typically comprises a population of cells, cellular extract, subcellular component, proteins, peptides, tissue culture, tissue, a bodily fluid, or a portion or combination thereof. When multiple targets are detected a pooled subset of immuno-labeled complexes are formed and incubated with the sample or individual subsets are add sequentially to a sample. For methods using flow cytometry the population of cells is illuminated when they pass through an optical examination zone and the data collected about the label determines the identity and quantity of the targets.

DETAILED DESCRIPTION OF THE INVENTION

I. Definitions

Figure 1:
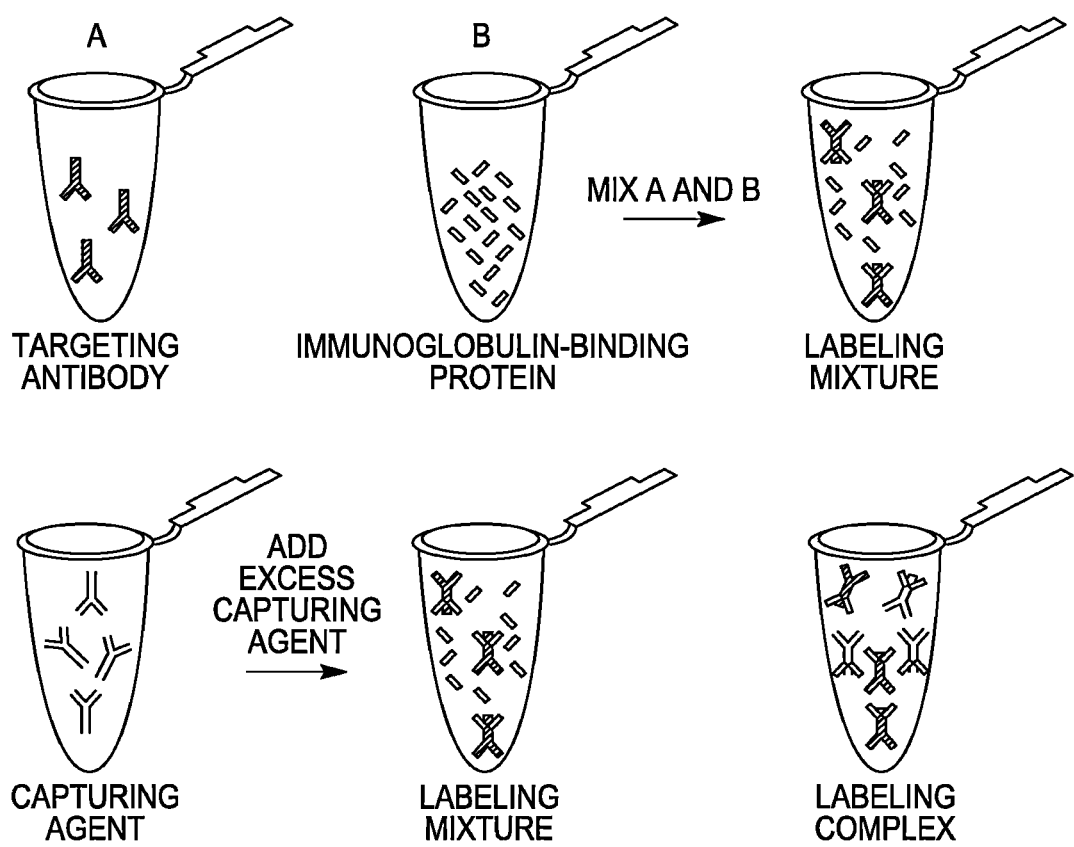
FIG. 1: Shows a schematic representation of the formation of the immuno-labeled complex (target-binding antibody and labeling reagent).

Before describing the present invention in detail, it is to be understood that this invention is not limited to specific compositions or process steps, as such may vary. It should be noted that, as used in this specification and the appended claims, the singular form "a", "an" and "the" include plural referents unless the context clearly dictates otherwise. Thus, for example, reference to "a protein labeling complex" includes a plurality of complexes and reference to "a target-binding protein" includes a plurality of proteins and the like.

Unless defined otherwise, all technical and scientific terms used herein have the same meaning as commonly understood by one of ordinary skill in the art to which this invention is related. The following terms are defined for purposes of the invention as described herein.

The term "affinity" as used herein refers to the strength of the binding interaction of two molecules, such as an antibody and an antigen or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "High affinity" refers to a ligand that binds to an antibody having an affinity constant ($K_a$) greater than $10^4$ $M^{-1}$, typically $10^5$-$10^{11}$ $M^{-1}$; as determined by inhibition ELISA or an equivalent affinity determined by comparable techniques such as, for example, Scatchard plots or using $K_d$/dissociation constant, which is the reciprocal of the $K_a$, etc.

The term "antibody" as used herein refers to a protein of the immunoglobulin (Ig) superfamily that binds noncovalently to certain substances (e.g. antigens and immunogens) to form an antibody-antigen complex. Antibodies can be endogenous, or polyclonal wherein an animal is immunized to elicit a polyclonal antibody response or by recombinant methods resulting in monoclonal antibodies produced from hybridoma cells or other cell lines. It is understood that the term "antibody" as used herein includes within its scope any of the various classes or sub-classes of immunoglobulin derived from any of the animals conventionally used.

The term "antibody fragments" as used herein refers to fragments of antibodies that retain the principal selective binding characteristics of the whole antibody. Particular fragments are well-known in the art, for example, Fab, Fab', and F(ab')$_2$, which are obtained by digestion with various proteases, pepsin or papain, and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH1 domains; (ii) the dAb fragment (Ward, et al., Nature 341, 544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

The term "antigen" as used herein refers to a molecule that induces, or is capable of inducing, the formation of an antibody or to which an antibody binds selectively, including but not limited to a biological material. Antigen also refers to "immunogen". The target-binding antibodies selectively bind an antigen, as such the term can be used herein interchangeably with the term "target".

The term "anti-region antibody" as used herein refers to an antibody that was produced by immunizing an animal with a select region that is a fragment of a foreign antibody wherein only the fragment is used as the immunogen. Anti-region antibodies include monoclonal and polyclonal antibodies. The term "anti-region fragment" as used herein refers to a monovalent fragment that was generated from an anti-region antibody of the present invention by enzymatic cleavage.

The term "biotin" as used herein refers to any biotin derivative, including without limitation, substituted and unsubstituted biotin, and analogs and derivatives thereof, as well as substituted and unsubstituted derivatives of caproylamidobiotin, biocytin, desthiobiotin, desthiobiocytin, iminobiotin, and biotin sulfone.

The term "biotin-binding protein" as used herein refers to any protein that binds selectively and with high affinity to biotin, including without limitation, substituted or unsubstituted avidin, and analogs and derivatives thereof, as well as substituted and unsubstituted derivatives of streptavidin, ferritin avidin, nitroavidin, nitrostreptavidin, and Neutravidin™ avidin (a de-glycosylated modified avidin having an isoelectric point near neutral).

The term "buffer" as used herein refers to a system that acts to minimize the change in acidity or basicity of the solution against addition or depletion of chemical substances.

The term "capture reagent" refers to a non-specific immunoglobulin that is used to remove excess labeling reagent after the formation of the immuno-labeled complex. The capture reagent is optionally attached a matrix to facilitate removal of the excess labeling regent. A matrix typically includes a microsphere, an agarose bead or any solid surface that the excess labeling reagent can be passed by.

The term "chromophore" as used herein refers to a label that emits light in the visible spectra that can be observed without the aid of instrumentation.

The term "complex" as used herein refers to the association of two or more molecules, usually by non-covalent bonding, e.g., the association between an antibody and an antigen or the labeling reagent and the target-binding antibody.

The term "detectable response" as used herein refers to an occurrence of, or a change in, a signal that is directly or indirectly detectable either by observation or by instrumentation. Typically, the detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

The term "detectably distinct" as used herein refers to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in the sample, as well as from additional materials that are optionally present.

The term "directly detectable" as used herein refers to the presence of a material or the signal generated from the material is immediately detectable by observation, instrumentation, or film without requiring chemical modifications or additional substances.

The term "examination zone" as used herein refers to an optical zone of a flow cytometer, or a similar instrument, wherein cells are passed through essentially one at a time in a thin stream whereby the bound immuno-labeled complex is illuminated and the intensity and emission spectra of the fluorophore is detected and recorded. This includes instruments wherein the examination zone moves and the sample is held in place.

The term "fluorophore" as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, September 2002).

The term "immuno-labeled complex" refers to the complex of target-binding antibody that is non-covalently attached to a labeling reagent.

The term "immuno-labeled complex subset" as used herein refers to a discrete set of immuno-labeled complexes that are homogenous and can be distinguished from another subset of immuno-labeled complex by the physical properties of the label, or the ratio of the label to labeling reagent, or the ratio of labeling reagent to target-binding antibody, or the target-binding antibody. Typically an immuno-labeled complex subset is present in a buffer to provide a "target detection solution".

The term "kit" as used herein refers to a packaged set of related components, typically one or more compounds or compositions.

The term "label" as used herein refers to a chemical moiety or protein that retains it's native properties (e.g. spectral properties, conformation and activity) when attached to a labeling reagent and used in the present methods. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (9th edition, CD-ROM, September 2002), supra.

The term "labeling reagent" as used herein refers to a monovalent antibody fragment or a non-antibody monomeric protein provided that the labeling reagent has affinity for a selected region of the target-binding antibody and is covalently attached to a label.

The term "labeling reagent subset" as used herein refers to a discrete set of labeling reagents that are homogenous and can be distinguished from another subset of labeling reagent either by the physical properties of the label or the ratio of the label to labeling reagent.

The term "labeling solution" as used herein refers to a solution that is used to form an immuno-labeled complex wherein the solution comprises labeling reagents and a buffer.

The term "matrix" as used herein refers to a solid or semi-solid surface that a biological molecule can be attached to, such as a sample of the present invention or a capture reagent. Examples include, but are not limited to, agarose, polyacrylamide gel, polymers, microspheres, glass surface, plastic surface, membrane, margnetic surface, and an array.

The term "monovalent antibody fragment" as used herein refers to an antibody fragment that has only one antigen-binding site. Examples of monovalent antibody fragments include, but are not limited to, Fab fragments (no hinge region), Fab' fragments (monovalent fragments that contain a heavy chain hinge region), and single-chain fragment variable (ScFv) proteins.

The term "non-antibody monomeric protein" as used herein refers to a protein that binds selectively and non-covalently to a member of the Ig superfamily of proteins, including but not limited to proteins A, G, and L, hybrids thereof (A/G), recombinant versions and cloned versions thereof, fusions of these proteins with detectable protein labels, and lectins but the protein itself is not an antibody or an antibody fragment.

The terms "protein" and "polypeptide" are used herein in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

The term "purified" as used herein refers to a preparation of a target-binding antibody that is essentially free from contaminating proteins that normally would be present in association with the antibody, e.g., in a cellular mixture or milieu in which the protein or complex is found endogenously such as serum proteins or hybridoma supernatant.

The term "sample" as used herein refers to any material that may contain a target, as defined below. Typically, the sample comprises a population of cells, cellular extract, sub-cellular components, tissue culture, a bodily fluid, and tissue. The sample may be in an aqueous solution, a viable cell culture or immobilized on a solid or semi solid surface such as a gel, a membrane, a glass surface, a microparticle or on a microarray.

The term "target" as used herein refers to any entity that a target-binding antibody has affinity for such as an epitope or antigen. This target includes not only the discrete epitope that the target-binding antibody has affinity for but also includes any subsequently bound molecules or structures. In this way an epitope serves as a marker for the intended target. For example, a cell is a target wherein the target-binding antibody binds a cell surface protein such as CD3 on a T cell wherein the target marker is CD3 and the target is the T cell.

The term "target-binding antibody" as used herein refers to an antibody that has affinity for a discrete epitope or antigen that can be used with the methods of the present invention. Typically the discrete epitope is the target but the epitope can be a marker for the target such as CD3 on T cells. The term can be used interchangeably with the term "primary antibody" when describing methods that use an antibody that binds directly to the antigen as opposed to a "secondary antibody" that binds to a region of the primary antibody.

II. Compositions and Methods of Use

In accordance with the present invention, labeling reagents, methods for labeling target-binding antibodies and methods for using the labeled antibodies to detect a target in a sample are provided. The labeling reagents comprise monovalent antibody fragments or non-antibody monomeric proteins that are covalently attached to a label of the present invention. The label covalently attached to a labeling reagent is directly detectable such as a fluorophore or functions as an indirect label that requires an additional component such as a colorimetric enzyme substrate or an enzyme conjugate. The labeling reagents have affinity for a specific region of the target-binding antibody. The target-binding antibodies are defined as any antibody known to one skilled in the art that has an affinity for a target in a sample. The target-binding antibodies are labeled with the labeling reagent in a labeling method to form immuno-labeled complexes and then added to a sample to detect a target.

The labeling reagent and the methods of the present invention provide for detection of one or multiple targets in a sample. Multiple targets are detected when either pooled subsets of immuno-labeled complexes or a panel of subsets that are sequentially added to a sample. The subset of immuno-labeled complexes begins with labeling reagent subsets wherein a labeling reagent subset is distinguished by the ratio of label to labeling reagent or by the physical characteristics of the label. The discrete labeling reagents subsets are added to the target-binding antibodies wherein the affinity of the antibody and ratio of labeling reagent to target-binding antibody determines the subsets of immuno-labeled complexes. This results in an infinite number of immuno-labeled complex subsets that are distinguished by i) the target-binding antibody, or ii) a ratio of label to labeling reagent, or iii) a ratio of labeling reagent to the target-binding antibody or iv) by a physical property of the label. These subsets can be used individually in a method of the present invention to detect a single or multiple targets in a sample or pooled and used to simultaneously detect multiple targets in a sample. These pooled subsets allow for not only detection but also identification and quantitation of the targets.

A. Labeling Reagents

1. Monovalent Antibody Fragments and Monomeric Non-Antibody Proteins

The labeling reagents of the present invention are monovalent antibody fragments or non-antibody monomeric proteins that have affinity for a region of a target-binding antibody. The regions of the target-binding antibody that can be bound by a labeling reagent include the Fc region, the kappa or lambda light chain region or a heavy chain region. When the labeling reagent is derived from an antibody the monovalent fragment can be, anti-Fc, an anti-Fc isotype, anti-kappa light chain, anti-lambda light chain, or a single-chain fragment variable protein. Labeling reagents that are a non-antibody peptide or protein, are for example but not limited to, soluble Fc receptor, protein G, protein A, protein L, lectins, or a fragment thereof. The labeling reagents typically have affinity for the Fc region of the target-binding antibody but any region, except the binding domain, may be used as a binding site for the labeling reagent. The Fc region is preferable because it is the farthest from the binding domain of the target-binding antibody and is unlikely to cause steric hinderance, when bound by a labeling reagent, of the binding domain for the target.

Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate anti-species antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds). When IgG is treated with the enzyme papain, a monovalent antigen-binding fragment can be isolated, referred herein to as a Fab fragment. When IgG is treated with pepsin (another proteolytic enzyme), a larger fragment is produced, F(ab')$_2$. This fragment can be split in half by treating with a mild reducing buffer that results in the monovalent Fab' fragment. The Fab' fragment is slightly larger than the Fab and contains one or more free sulfhydryls from the hinge region (which are not found in the smaller Fab fragment). The term "antibody fragment" is used herein to define both the Fab' and Fab portions of the antibody. It is well known in the art to treat antibody molecules with pepsin and papain in order to produce antibody fragments (Gorevic et al., Methods of Enzyol., 116:3 (1985)).

The monovalent Fab fragments of the present invention are produced from either murine monoclonal antibodies or polyclonal antibodies generated in a variety of animals that have been immunized with a foreign antibody or fragment thereof, U.S. Pat. No. 4,196,265 discloses a method of producing monoclonal antibodies. Typically, labeling reagents are derived from a polyclonal antibody that has been produced in a rabbit or goat but any animal known to one skilled in the art to produce polyclonal antibodies can be used to generate anti-species antibodies. However, monoclonal antibodies are equal, and in some cases, preferred over polyclonal antibodies provided that the target-binding antibody is compatible with the monoclonal antibodies that are typically produced from murine hybridoma cell lines using methods well known to one skilled in the art. Example 1 describes production of polyclonal antibodies raised in animals immunized with the Fc region of a foreign antibody. It is a preferred embodiment of the present invention that the labeling reagents be generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or pa pain, to produce monovalent fragments. The fragments are then affinity purified on a column comprising whole immunoglobulin protein that the animal was immunized against or just the Fc fragments. As described in detail below, the labeling reagents are also covalently labeled with fluorophore labels when bound to the affinity column to eliminate incorporating label into the binding domain of the monovalent fragment. One of skill in the art will appreciate that this method can be used to generate monovalent fragments against any region of a target-binding protein and that selected peptide fragments of the target-binding antibody could also be used to generate fragments.

Alternatively, a non-antibody protein or peptide such as protein G, or other suitable proteins, can be used alone or coupled with albumin wherein albumin is attached with a label of the present invention. Preferred albumins of the invention include human and bovine serum albumins or ovalbumin. Protein A, G and L are defined to include those proteins know to one skilled in the art or derivatives thereof that comprise at least one binding domain for IgG, i.e. proteins that have affinity for IgG. These proteins can be modified but do not need to be and are labeled in the same manner as the monovalent Fab fragments of the invention.

2. Labels

The labels of the present invention include any directly or indirectly detectable label known by one skilled in the art that can be covalently attached to the labeling reagent of the present invention. Labels include, without limitation, a chromophore, a fluorophore, a fluorescent protein, a phosphorescent dye, a tandem dye, a particle, a hapten, an enzyme and a radioisotope. Preferred labels include fluorophores, fluorescent proteins, haptens, and enzymes.

A fluorophore of the present invention is any chemical moiety that exhibits an absorption maximum beyond 280 nm, and when covalently attached to a labeling reagent retains its spectral properties. Fluorophores of the present invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Preferred fluorophores of the invention include xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore attached to the labeling reagent will determine the absorption and fluorescence emission properties of the labeling reagent and immuno-labeled complex. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Many of fluorophores can also function as chromophores and thus the described fluorophores are also preferred chromophores of the present invention.

In addition to fluorophores, enzymes also find use as labels for the labeling reagents. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. colorimetric, fluorescent or chemiluminescence. Such substrates are extensively used in the art, many of which are described in the MOLECULAR PROBES HANDBOOK, supra.

A preferred colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931) and dihydrorhodamines including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In addition to enzymes, haptens such as biotin are also preferred labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

Fluorescent proteins also find use as labels for the labeling reagents of the present invention. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorphore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in U.S. Pat. No. 5,798,276, or the sulfonated cyanine fluorophores disclosed in U.S. Ser. Nos. 09/968/401 and 09/969/853; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

3. Covalent Attachment of Labels to the Labeling Reagents

The labeling reagents can be independently attached to one or more labels of the present invention by a number of methods known to one skilled in the art and modification of such methods. Methods include, labeling in a solution or on an affinity column. For labeling in solution the labeling reagent is optionally modified to contain a reactive group and the label is modified to contain a reactive group or is synthesized to contain a reactive group, as is typically the case with fluorophore labels wherein the reactive group facilitates covalent attachment. The modification of the labeling reagent to contain a reactive group includes (1) chemical addition of such a reactive group or (2) alternatively takes advantage of the disulfide bonds of the F(ab')$_2$ fragment wherein the fragment is reduced to break the bond and expose the thiol group that readily reacts with a reactive group on a label, as disclosed in U.S. Pat. No. 5,360,895. Typically, covalent attachment of the label to the fragment is the result of a chemical reaction between an electrophilic group and a nucleophilic group. However, when a label is used that is photoactivated the covalent attachment results when the labeling solution is illuminated.

A method for covalently attaching a label, particularly an enzyme, a fluorescent protein or a particle, comprises the following steps:
 a) cleaving an intact anti-region antibody with an enzyme resulting in a F(ab')$_2$ fragment;
 b) contacting said F(ab')$_2$ fragment with a reducing agent to produce Fab' fragments containing a thiol group;
 c) contacting said Fab' fragments with a solution comprising a label that contains a reactive group; and,
 d) isolating Fab' fragments of step d) that are covalently attached to a label by size exclusion or affinity chromatography.

The whole anti-region antibody is cleaved with pepsin to generate a bivalent F(ab)'$_2$ fragment. This fragment is typically affinity purified on a column comprising immunoglobulin proteins such as IgG that is immobilized in agarose. The fragment is then reduced to break the disulfide bond of the hinge region that connects the two Fab fragments resulting in a Fab' fragment with an exposed thiol group. This is typically accomplished by adding a mild reducing buffer to the affinity purified F(ab)$_2$ fragments such as a buffer comprising 0.01 M EDTA and 0.01 M cysteine in phosphate buffer saline (PBS). The resulting thiol group readily reacts with a reactive group on a label to covalently attach the label to the fragment. Thus, a solution containing a label that has been chemically modified to contain a reactive group, using methods well known to one skilled in the art, is added to the solution of reduced Fab' fragments. This method is particularly useful for covalently attaching enzyme and other protein labels due to their size and the lack of exposed amine groups on the Fab fragments. One of skill in the art will appreciate that this method requires the use of Fab' fragments as apposed to Fab fragments due to the disulfide bonds of the Fab' fragment and that the use of the enzyme papain or the like results in such a fragment.

An alternative labeling of monovalent antibody fragments and the monomeric non-antibody proteins is also accomplished in a solution. The method comprises the steps:
 a) contacting a Fab fragment or non-antibody monomeric protein with a solution comprising a label that contains a reactive group; and,
 b) isolating labeled anti-region Fab fragment or non-antibody monomeric protein by size exclusion or affinity chromatography.

When a Fab fragment is to be labeled the whole antibody is cleaved with an enzyme, such as papain, to generate Fab monovalent fragments and the fragments are typically purified on an affinity column prior to addition of the label. The Fab fragment or non-antibody monomeric proteins are optionally chemically modified to contain a reactive group. However, for covalently attaching reactive fluorophore labels it has been found that this modification of the fragment of non-antibody protein is not necessary. The reactive label, typically a fluorophore or hapten, are added to a solution of Fab fragments or non-antibody proteins and the labeling reagent is separated from excess label by size exclusion or affinity chromatorgraphy. The labeling reagents are then stored in an appropriate buffer.

Labeling in solution can have some drawbacks, especially when labeling of Fab fragments or non-antibody proteins with fluorophores. Thus, Fab fragments and non-antibody proteins of the present invention are preferably covalently attached to a fluorophore label when immobilized on an affinity column. The fragments and non-antibody proteins are immobilized on an affinity column that comprises a protein that the fragment has affinity for, typically IgG, and after immobilization a reactive fluorophore is added to the column wherein the fragments are labeled and unreacted fluorophores pass through the column.

The use of this affinity chromatography method avoids the incorporation of label into the binding domain of the Fab fragment or non-antibody protein. When Fab fragments are labeled with fluorophores using this method unexpected advantages were obtained wherein the fluorescent signal form fragments labeled on a column are brighter than fragments labeled in solution when the fluorophore and ratio of fluorophore to labeling reagent are held constant. Without wishing to be bound by a theory it is possible that the decreased brightness observed from the fragments labeled in solution is due to quenching of fluorphores that are bound in or near the binding domain by the high concentration of amine groups in the binding domain. Thus, a preferred embodiment of the invention for covalently attaching fluorphore labels to Fab fragments comprises the following steps:
  a) cleaving an intact anti region antibody with an enzyme that generates Fab fragments;
  b) isolating the anti-region Fab fragments of step a);
  c) contacting a matrix comprising intact immunoglobulin proteins or fragments thereof that specifically bind anti-region Fab fragments with a solution comprising said anti-region fragments of step b) wherein said Fab fragments are immobilized;
  d) contacting said matrix of step c) with a solution comprising a fluorophore label that contains a reactive group;
  e) washing said matrix to remove unbound label, and;
  f) eluting said labeling reagent from said matrix whereby said labeling reagent is manufactured comprising a label and being isolated from other proteins and fragments thereof.

The matrix is typically an agarose column that comprises either the selected region, such as the Fc region, or the entire antibody provided that the antibody or fragment thereof is the same species and isotype that was used to produce the antibodies that the labeling reagent was generated from. However any matrix known to one skilled in the art can be used that allows for immobilization of labeling reagent and removal following attachment of the fluorophore label. Fab and Fab' fragments can both be labeled in this manner. However a free thiol group is not necessary and therefore Fab fragments are typically labeled using this method.

Due to the unique properties of the labeling reagent and the attached labels it is a preferred embodiment of the present invention that enzyme or other protein labels are covalently attached to Fab' fragments in solution utilizing the free thiol group of the Fab' fragment. It is another preferred embodiment that fluorophore labels be covalently attached to the labeling reagent when the reagent is immobilized on a affinity column wherein the labeling reagent is typically an Fab fragment or a non-antibody monomeric protein.

The attachment of the label to the fragments or the non-antibody proteins results in multiple subsets that are distinguished by the ratio of the label to the labeling reagent and the physical properties of the label. A labeling reagent subset as used herein refers to a discrete set of labeling reagents that are homogenous and can be distinguished from another subset of labeling reagent either by the physical properties of the label or the ratio of the label to labeling reagent. The physical properties include differences within a group of labels, such as emission spectra of fluorophores, or across groups of labels, such as the difference between an enzyme and a fluorophore. For fluorphore labels, the physical properties typically relates to the emission spectra, this includes modification of the same label, e.g. a cyanine with different substitutions that shifts the emission wavelength, or different fluorophores, e.g. a cyanine and a coumarin on the same labeling reagent. The difference in physical properties also includes the use of tandem dyes, which is specifically defined to include an energy transfer pair wherein one is a protein and the other is a fluorophore or both are fluorophores, or the pairing of other labels that are not necessarily energy transfer pairs. A few examples of labeling reagent subsets includes, but are not limited to, a first subset comprising a single fluorophore at a known ration attached to a anti-Fc Fab fragment; a second subset comprises the same fluorophore on the Fab fragment at a different known ration from the first subset, a third subset comprises the same fluorophore but that has a shifted wavelength due to a substitution on the fluorophore. Thus, the attachment of labels to the labeling reagents results in an extensive selection of subsets that when complexed with a target-binding antibody results in a unique method to detect one or multiple targets in a sample whereby the target is identified and quantitated.

B. Immuno-Labeled Complex

The subsets of labeling reagent are complexed with target-binding antibodies to produce subsets of immuno-labeled complex that for the target detection solution. The methods for forming the immuno-labeled complex comprises the following steps:
  a) contacting a solution of target-binding antibodies with a labeling reagent subset, wherein said labeling reagent subsets are distinguished by i) ratio of label to labeling reagent or ii) a physical properties of said label;
  b) incubating said target-binding antibodies and said labeling reagent for a time period sufficient for one or more labeling reagents to form an immuno-labeled complex with a target-binding antibody wherein a region of said target binding antibody is selectively bound by labeling reagent;
  c) optionally removing unbound labeling reagent by adding a capture reagent comprising immunoglobulin proteins or fragments thereof; and,
  d) optionally repeating said steps a), b), and c) to form individual or pooled subsets of immuno-labeling complexes wherein each subset is distinguished from another subset by i) a ratio of label to labeling reagent, or ii) a physical property of said label, or iii) a ratio of labeling reagent to said target-binding antibody, or iv) by said target-binding antibody.

A particular advantage for the use of labeling reagent of the present invention to label target-binding antibodies is that the process is relatively insensitive to the solution the antibodies are in. Due to the physical nature of the labeling reagents, small monovalent fragments, the reagents do not cross-link and fall out of solution in the presence of high concentration of proteins. For this reason, target-binding antibodies can be complexed when present in ascites fluid, tissue culture supernatant, serum or other solutions where there is a high concentration of proteins. This eliminates the need to purify target-binding proteins prior to labeling.

When preparing the immuno-labeled complex using purified target-binding antibody, stock solutions of both the labeling reagent and the target-binding antibody are typically near 1 mg/mL in an appropriate buffer, although more or less concentrated solutions are also suitable. Generally, the labeling reagent is mixed in a molar ratio of at least one to 50 moles of labeling reagent to one mole of the target-binding antibody to be complexed. More commonly a ratio of at least one to as many as 10 moles of labeling reagent per mole of target-binding antibody is combined. With an anti-Fc region Fab to a target-binding antibody, a molar ratio of approximately 2 to 10 is typical, more typically 3 to 5 (particularly for complexes in which the labeling reagent has been labeled while immobilized on an affinity matrix). The ease of formation of the complex permits rapid optimization of the complex and assessment of the effect of variation in experimental parameters. A particularly unique advantage of the invention is that the stoichiometry of the complex is easily adjusted to provide complexes with different ratios of labeling reagent to target-binding antibody, and thus there is control over the ultimate detectability of the target in the sample. Complexes that have been labeled with the same dye but at different molar ratios can be separately detected by the differences in their intensities.

Complex formation appears to occur almost within the mixing time of the solutions (<1 minute) but the reaction typically is allowed to proceed for at least 5 minutes and can be longer before combining the immuno-labeled complex with the sample. Although complex formation can be reversed by addition of an unlabeled antibody that contains the same binding region, reversibility is very slow; furthermore, following binding of the immuno-labeled complex to a target in a sample, the sample can be "fixed" using aldehyde-based fixatives by methods that are commonly practiced by those skilled in the art of immunolabeling.

The labeling process optionally further comprises the addition of a capture component to remove excess labeling reagent. For applications in which immunolabeling complexes of multiple primary antibodies from the same species (e.g. mouse monoclonal antibodies) or cross-reacting species (e.g. mouse and human antibodies) are to be used simultaneously or sequentially, it is necessary to quench or otherwise remove any excess labeling reagent by use of a capture component or by other means to avoid inappropriate labeling of the sample. The most effective capturing components to capture excess labeling reagent are those that contain the binding site of the labeling reagent but are themselves not labeled, preferably an antibody or antibody fragment. Capture components may be free in solution or immobilized on a matrix, such as agarose, cellulose, or a natural or synthetic polymer, to facilitate separation of the excess capture component from the immuno-labeled complex. The capture component is optionally attached to a microsphere or magnetic particle. However, separation of excess labeling reagent is not essential for successful utilization of the invention, particularly when using a single target-binding antibody.

The steps of the labeling process for the target-binding antibodies can be repeated to form discrete immuno-labeled complex subsets that can be used individually or pooled in an assay to detect individual or multiple targets. As used herein the term immuno-labeled complex subsets refers to subsets that are distinguished from each other i) a ratio of label to labeling reagent, or ii) a physical property of the label, or iii) a ratio of labeling reagent to the target-binding antibody, or iv) by the target-binding antibody, or a combination thereof. For example a panel of subsets may comprise a target-binding antibody that is bound by a labeling reagent comprising a subset of different ratios of the same label on the labeling reagent resulting in a discrete subset of immuno-labeled complexes. This subset of immuno-labeled complexes can be used individually wherein a target is identified by the intensity of the detectable label or used in combination with another subset of immunocomplexes that differ in the target-binding antibody to identify multiple targets.

C. Methods of Use

The labeling reagents, target-binding antibodies and resulting immuno-labeled complex that forms the target detection solution can be used in a wide range of immunoassays, essentially in any assay a traditional secondary antibody is used including some assays that secondary antibodies are not used because of their size and ability to cross-link. Examples of such assays used to detect a target in a sample include immunoblots, direct detection in a gel, flow cytometry, immunohistochemistry, confocal microscopy, fluorometry, ELISA and other modified immunoassays.

A method of the present invention for detecting a single target in a sample comprises the following steps:
 a) contacting a solution of target-binding antibodies with a labeling reagent subset, wherein said labeling reagent subsets are distinguished by i) ratio of label to labeling reagent or ii) a physical properties of said label;
 b) incubating said target-binding antibodies and said labeling reagent subset for a time period sufficient for one or more labeling reagents to form an immuno-labeled complex with a target-binding antibody wherein a region of said target binding antibody is selectively bound by labeling reagent;
 c) contacting said sample with said immuno-labeled complex of step b);
 d) incubating said sample of step c) for a time sufficient to allow said immuno-labeled complex to selectively bind to said target; and,
 e) illuminating said immuno-labeled complex whereby said target is detected.

A sample is incubated with a preformed immuno-labeled complex that comprises a labeling reagent and a target-binding antibody. While this method describes the identification of a single target, subsets of labeling reagents bound to the same target-binding antibody can be used to identify and provide additional information about such targets. For example, subsets of labeling reagent can be prepared wherein two discrete subsets are generate each with a distinct fluorophore label that is distinguished by their emission spectra, e.g. one that emits in the green spectra and one that emits in the red spectra. The labeling reagent subsets are then added to a solution of target-binding antibody in a controlled ratio, e.g. two parts one labeling reagent (green emission) and one part the other labeling reagent (red emission) per target binding antibody. In this way the immuno-labeled complexes can be used to detect a target. If another immuno-labeled complex were added to the sample the original target could be distinguished from the subsequently detected target.

The methods of the present invention also provide for the detection of multiple targets in a sample. Multiple targets include the discrete epitope that the target-binding antibody has affinity for as well as molecules or structures that the epitope is bound to. Thus, multiple target identification includes phenotyping of cells based on the concentration of the same cell surface marker on different cells. In this way multiple target identification is not limited to the discrete epitope that the target binding antibody binds, although this is clearly a way that multiple targets can be identified, i.e. based on the affinity of the target-binding antibody.

Therefore, a method for detecting multiple targets in a sample comprises the following steps:
 a) contacting a solution of target-binding antibodies with a labeling reagent subset, wherein said labeling reagent subsets are distinguished by i) ratio of label to labeling reagent or ii) a physical properties of said label;
 b) incubating said target-binding antibodies and said labeling reagent subset for a time period sufficient for one or more labeling reagents to form an immuno-labeled complex with a target-binding antibody wherein a region of said target-binding antibody is selectively bound by labeling reagent, wherein steps a) and b) are repeated to form discrete immuno-labeling complex subsets;
 c) contacting said sample with a solution comprising A) a pooled subset of immuno-labeled complexes, wherein each subset is distinguished from another subset by i) a ratio of label to labeling reagent, or ii) a physical property of said label, or iii) a ratio of labeling reagent to said target-binding antibody, or iv) by said target-binding antibody or B) an individual subset wherein step c) with a solution comprising an individual subset is repeated;
 d) incubating said sample of step c) for a time sufficient to allow said immuno-labeled complex to selectively bind to said target; and,
 e) illuminating said immuno-labeled complex whereby said target is detected.

A selected target-binding antibody and a subset of labeling reagent are incubated to form an immuno-labeled complex subset. This procedure is repeated to form a panel of immuno-labeled complex subsets that may be pooled and added to a sample. Alternatively each immuno-labeled complex subset is added stepwise to a sample. The immuno-labeled complex subsets are distinguished by four characteristics resulting in an infinite number of immuno-labeled complex subsets. First (i) the subsets can be distinguished by the target-binding antibody that is determined by the end user for the information that is desired from a sample. This means that each subset is distinguished based on the affinity of the target-binding antibody. The target-binding antibody typically distinguishes immuno-labeled complexes when multiple targets are identified, however this is normally combined with another characteristic to gain information form a sample or increase the number of targets that can be detected at one time. The second (ii) distinguishing feature used is the ratio of label to labeling reagent, as discussed in detail above. A subset based on this feature would have for example a ratio of two fluorophore per each labeling reagent. The third (iii) distinguishing feature is the ratio of labeling reagent to target-binding antibody. This is accomplished using a controlled concentration of target-binding antibody mixed with a controlled concentration of a labeling reagent subset and the subset would comprise a target-binding antibody that is bound by a discrete number of labeling proteins. The fourth (iv) feature is the physical feature of the label. Typically this refers to the physical properties of the fluorophore labels wherein a subset of this group is distinguished by the label itself such as a green emitting fluorophore compared to a red emitting fluorophore. One of skill in the art will appreciate that while immuno-labeling complex subsets can be distinguished based on one feature the subsets are typically, and most useful, when discretely identified based on a combination of the distinguishing characteristics.

Another example of detection of multiple targets utilizes the following immuno-labeled subsets, all of which comprise a different target-binding antibody but differ in the label and ratio of label. The first subset comprises a fluorophore label that emits red-fluorescent light, a second subset comprises a fluorophore label that emits green fluorescent light, a third subset comprises a ratio of 1:1 red to green fluorophore label; a fourth subset comprises a ratio of 2:1 red to green fluorophore label and a fifth subset comprises a ratio of 1:2 red to green fluorophore label. These subsets allow for the simultaneous detection of five targets in a sample. This aspect of the present invention is particularly important due to the limited range of fluorophores available wherein the labeling reagents can be utilized to increase the number of targets that can be detected at one time. One of skill in the art can appreciate that these subsets could be expanded by altering the ratio of label to labeling reagent instead of just the ratio of labeling reagent to target-binding antibody. This same methodology can also be applied to a single fluorophore label wherein the ratios are altered and a target is detected based on the intensity of the signal instead of the color and the ratio of the color to another color.

Following the formation of the immuno-labeled complex subsets the subsets can be pooled and added to a sample or added stepwise to a sample, either of which is determined by the end user and the particular assay format. This method of the present invention provides for maximum flexibility and ease of determining multiple targets in a sample.

Another method of the present invention provides for the determination of multiple targets in a sample specifically using the flow cytometry assay format. Traditionally targets identified using flow cytometry used either directly labeled primary antibody or labeled microspheres that were covalently attached to a primary antibody wherein the microsphere is the label. Examples include the fluorescent encapsulated microsphere beads sold by Luminex. The labeling reagents and the present invention overcome both the need for directly labeled primary antibody and the need for expensive microspheres.

Thus, a method of the present invention for determining identity and quantity of targets in a sample by detecting multiple targets comprises the following steps:
    a) contacting a solution of target-binding antibodies with a labeling reagent subset, wherein said labeling reagent subsets are distinguished by i) ratio of label to labeling reagent or ii) a physical properties of said label;
    b) incubating said target-binding antibodies and said labeling reagent for a time period sufficient for one or more labeling reagents to form an immuno-labeled complex with a target-binding antibody wherein a region of said target binding antibody is selectively bound by labeling reagent, wherein steps a) and b) are repeated to form a pooled subset of immuno-labeling complexes;
    c) contacting a population of cells in a sample with a solution comprising a pooled subset of immuno-labeled complexes, wherein each subset is distinguished from another subset by i) a ratio of label to labeling reagent, or ii) a physical property of said label, or iii) a ratio of labeling reagent to said target-binding antibody, or iv) by said target-binding antibody;
    d) incubating said cells for a time period sufficient to allow said immuno-labeled complex to bind said targets;
    e) passing said incubated population of cells through an examination zone; and,
    f) collecting data from said cells that were passed through said examination zone wherein said multiple targets are detected whereby the identity and quantity of said targets is determined.

In one aspect, a target-binding antibody is pre-complexed to the target-binding antibody to form a subset and that subset or a panel of subsets are added to a sample, that are typically distinguished by the target binding antibody. This method then avoids the need for a directly labeled primary. Secondly, when the panel of subsets is distinguished, for example, by the ratio of label to labeling reagent or the ratio of labeling reagent to target-binding antibody the immuno-labeled complex can function similar to the microsphere beads of Luminex. For example, this is accomplished wherein three immuno-labeled complex subsets are distinguished by the target binding antibody and the fluorophore attached to the labeling reagent and within one of the subsets is another set of subsets that are distinguished based on the ratio of label to labeling reagent. In this way three different epitopes are detected and one of the epitopes is further distinguished and a phenotype distinction made based on the intensity of the signal generated from the labeled-immuno complex subsets based on the ratio of fluorophore to labeling reagent. This determination of targets is facilitated when a population of cells or cellular organelles is passed through the examination zone of a flow cytometer wherein the fluorescent signal and intensity is recorded for each cell resulting in a histogram of the cell population or cellular organelles based on the detected epitopes.

In another aspect of the invention, additional detection reagents are combined with the sample concurrently with or following the addition of immuno-labeled complex subsets. Such additional detection reagents include, but are not limited to reagents that selectively detect cells or subcellular components, ions, or indicate the cell viability, life cycle, or proliferation state. For example, the additional detection reagent is a labeled target-binding antibody that is directly or indirectly detectable and another additional detection reagent is a stain for nucleic acids, for F-actin, or for a cellular organelle.

1. Sample Preparation

The sample is defined to include any material that may contain a target to which an antibody has affinity for. Typically the sample is biological in origin and comprises tissue, cell or a population of cells, cell extracts, cell homogenates, purified or reconstituted proteins, recombinant proteins, bodily and other biological fluids, viruses or viral particles, prions, subcellular components, or synthesized proteins. Possible sources of cellular material used to prepare the sample of the invention include without limitation plants, animals, fungi, bacteria, archae, or cell lines derived from such organisms. The sample can be a biological fluid such as whole blood, plasma, serum, nasal secretions, sputum, saliva, urine, sweat, transdermal exudates, cerebrospinal fluid, or the like. Alternatively, the sample may be whole organs, tissue or cells from an animal. Examples of sources of such samples include muscle, eye, skin, gonads, lymph nodes, heart, brain, lung, liver, kidney, spleen, solid tumors, macrophages, mesothelium, and the like.

Prior to combination with the immuno-labeled complexes, the sample is prepared in a way that makes the target, which is determined by the end user, in the sample accessible to the immuno-labeled complexes. Typically, the samples used in the invention are comprised of tissue, cells, cell extracts, cell homogenates, purified or reconstituted proteins, recombinant proteins, biological fluids, or synthesized proteins. Large macromolecules such as immuno-labeled complexes tend to be impermeant to membranes of live biological cells. Treatments that permeabilize the plasma membrane, such as electroporation, shock treatments, or high extracellular ATP, can be used to introduce the immuno-labeled complexes into cells. Alternatively, the immuno-labeled complexes can be physically inserted into cells, e.g. by pressure microinjection, scrape loading, patch-clamp methods, or phagocytosis. However, the desired target may require purification or separation prior to addition of the immuno-labeled complexes, which will depend on the way the antigenic determinants are contained in the sample. For example, when the sample is to be separated on a SDS-polyacrylamide gel the sample is first equilibrated in an appropriate buffer, such as a SDS-sample buffer containing Tris, glycerol, DTT, SDS, and bromophenol blue.

When the sample contains purified target materials, the purified target materials may still be mixtures of different materials. For example, purified protein or nucleic acid mixtures may contain several different proteins or nucleic acids. Alternatively, the purified target materials may be electrophoresed on gels such as agarose or polyacrylamide gels to provide individual species of target materials that may be subsequently blotted onto a polymeric membrane or detected within the gel matrix. Preparation of a sample containing purified nucleic acids or proteins generally includes denaturation and neutralization. DNA may be denatured by incubation with base (such as sodium hydroxide) or heat. RNA is also denatured by heating (for dot blots) or by electrophoresing in the presence of denaturants such as urea, glyoxal, or formaldehyde, rather than through exposure to base (for Northern blots). Proteins are denatured by heating in combination with incubation or electrophoresis in the presence of detergents such as sodium dodecyl sulfate. The nucleic acids are then neutralized by the addition of an acid (e.g., hydrochloric acid), chilling, or addition of buffer (e.g., Tris, phosphate or citrate buffer), as appropriate.

Preferably, the preparation of a sample containing purified target materials further comprises immobilization of the target materials on a solid or semi-solid support. Purified nucleic acids are generally spotted onto filter membranes such as nitrocellulose filters or nylon membranes in the presence of appropriate salts (such as sodium chloride or ammonium acetate) for DNA spot blots. Alternatively, the purified nucleic acids are transferred to nitrocellulose filters by capillary blotting or electroblotting under appropriate buffer conditions (for Northern or Southern blots). To permanently bind nucleic acids to the filter membranes, standard cross-linking techniques are used (for example, nitrocellulose filters are baked at 80° C. in vacuum; nylon membranes are subjected to illumination with 360 nm light). The filter membranes are then incubated with solutions designed to prevent nonspecific binding of the nucleic acid probe (such as BSA, casein hydrolysate, single-stranded nucleic acids from a species not related to the probe, etc.) and hybridized to probes in a similar solution. Purified proteins are generally spotted onto nitrocellulose or nylon filter membranes after heat and/or detergent denaturation. Alternatively, the purified proteins are transferred to filter membranes by capillary blotting or electroblotting under appropriate buffer conditions (for Western blots). Nonspecifically bound probe is washed from the filters with a solution such as saline-citrate or phosphate buffer. Filters are again blocked, to prevent nonspecific adherence of immuno-labeled complexes. Finally, samples are mixed with immuno-labeled complexes. Nonspecifically bound immuno-labeled complexes are typically removed by washing.

When the sample contains cellular nucleic acids (such as chromosomal or plasmid-borne genes within cells, RNA or DNA viruses or mycoplasma infecting cells, or intracellular RNA) or proteins, preparation of the sample involves lysing or permeabilizing the cell, in addition to the denaturation and neutralization already described. Cells are lysed by exposure to agents such as detergent (for example sodium dodecyl sulfate, Tween, sarkosyl, or Triton), lysozyme, base (for example sodium, lithium, or potassium hydroxide), chloroform, or heat. Cells are permeabilized by conventional methods, such as by formaldehyde in buffer.

As with samples containing purified target materials, preparation of the sample containing cellular target materials typically further comprises immobilization of the target materials on a surface such as a solid or semi-solid matrix. The targets may be arrayed on the support in a regular pattern or randomly. These supports include such materials as slides, polymeric beads including latex, optical fibers, and membranes. The beads are preferably fluorescent or nonfluorescent polystyrene, the slides and optical fibers are preferably glass or plastic, and the membrane is preferably poly(vinylidene difluoride) or nitrocellulose. Thus, for example, when the sample contains lysed cells, cells in suspension are spotted onto or filtered through nitrocellulose or nylon membranes, or colonies of cells are grown directly on membranes that are in contact with appropriate growth media, and the cellular components, such as proteins and nucleic acids, are permanently bound to filters as described above. Permeabilized cells are typically fixed on microscope slides with known techniques used for in situ hybridization and hybridization to chromosome "squashes" and "spreads," (e.g., with a reagent such as formaldehyde in a buffered solution). Alternatively, the samples used may be in a gel or solution.

In a particular aspect of the invention, the sample comprises of cells in a fluid, such as ascites, hybridoma supernatant, or serum, wherein the presence or absence of the target in such cells is detected by using an automated instrument that sorts cells according to the detectable fluorescence response of the detectable moieties in the immunolabeling complexes bound to such cells, such as by fluorescence activated cell sorting (FACS). For methods using flow cytometry a cell population typically comprises individually isolated cells that have been isolated from other proteins and connective tissue by means well known in the art. For example, lymphocyte cells are isolated from blood using centrifugation and a density gradient. The cells are washed and pelleted and the labeling solution added to the pelleted cells.

2. Illumination

At any time after addition of the immuno-labeled complex to the sample, the sample is illuminated with a wavelength of light selected to give a detectable optical response, and observed with a means for detecting the optical response. Equipment that is useful for illuminating the fluorescent compounds of the present invention includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The degree and/or location of signal, compared with a standard or expected response, indicates whether and to what degree the sample possesses a given characteristic, i.e. desired target.

The optical response is optionally detected by visual inspection, or by use of any of the following devices: CCD camera, video camera, photographic film, laser-scanning devices, fluorometers, photodiodes, quantum counters, epifluorescencea microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

When an indirectly detectable label is used then the step of illuminating typically includes the addition of a reagent that facilitates a detectable signal such as colorimetric enzyme substrate. Radioisotopes are also considered indirectly detectable wherein an additional reagent is not required but instead the radioisotope must be exposed to X-ray film or some other mechanism for recording and measuring the radioisotope signal. This can also be true for some chemiluminescent signals that are best observed after expose to film.

III. Kits of the Invention

Suitable kits for preparing an immuno-labeled complex and for detection of a target in a sample also form part of the invention. Such kits can be prepared from readily available materials and reagents and can come in a variety of embodiments. The contents of the kit will depend on the design of the assay protocol or reagent for detection or measurement. Generally, the kits will contain instructions, appropriate reagents and labels, and solid supports, as needed. Typically, instructions include a tangible expression describing the reagent concentration or at least one assay method parameter such as the relative amounts of reagent and sample to be admixed, maintenance time periods for reagent/sample admixtures, temperature, buffer conditions and the like to allow the user to carry out any one of the methods or preparations described above.

A preferred kit of the present invention comprises: a) a labeling solution comprising a labeling reagent that is independently attached to one or more labels and b) a solution comprising a capture reagent. A preferred embodiment of this kit provides a labeling reagent that is anti-Fc Fab fragment, protein G or protein G complexed with albumin. In a more particular embodiment of this kit, the capture component is purified mouse IgG or non-immune mouse serum and the albumin is human albumin, bovine serum albumin, or ovalbumin. In a more preferred embodiment the albumin is ovalbumin. The labeling solution is either a homogenous mixture of labeling reagents or comprises a pooled subset of labeling reagents. Alternatively the kit comprises a panel of labeling reagent subsets that can be used to make a subset of immunolabeled complexes.

Additionally the kits may comprise one or more additional components that include (a) stains for characterization of cellular organelles, cell viability, or cell proliferation state, (b) enzyme substrates or (c) enzyme conjugates such as avidin-HRP.

A wide variety of kits and components can be prepared according to the present invention, depending upon the intended user of the kit and the particular needs of the user. It is understood by one skilled in the art, that any of the labeling reagents contemplated by the present invention can be used to in a labeling solution to be included in a kit. The labeling reagents are not intended to be limited to only the described preferred embodiments.

IV. Applications

The instant invention has useful applications in basic research, high-throughput screening, immunohistochemistry, fluorescence in situ hybridization (FISH), microarray technology, flow cytometry, diagnostics, and medical therapeutics. The invention can be used in a variety of assay formats for diagnostic applications in the disciplines of microbiology, immunology, hematology and blood transfusion, tissue pathology, forensic pathology, and veterinary pathology. The invention is particularly useful in the characterization and selection of optimized antibodies from hybridoma supernatants. Additionally, the invention can be used to deliver therapeutics to a specific target. In general, the current invention provides a versatile and convenient method to enhance any assay that uses an antibody as part of its detection methodology.

The instant invention can be used to study biological phenomena, such as, for example, cell proliferation, signal transduction in cells, or apoptosis. For illustration purposes only and not limitation, one could study thymidine analog 5-bromo-2'-deoxyuridine (BrdU) incorporation. BrdU is a marker for both cell proliferation and apoptosis, as it is readily incorporated into newly synthesized DNA that has progressed through the S-phase of the cell cycle and also into DNA break sites by deoxynucleotidyl transferase (TdT). Anti-BrdU antibodies are used to detect cells marked by BrdU incorporation. By being able to directly label the anti-BrdU antibodies, the current invention provides a convenient method to allow for detection of the incorporated BrdU by conventional immunohistochemistry or fluorescence, depending on detection method required.

Additionally, the current invention has the advantage of allowing staining for multiple targets in one cocktail, thereby reducing the need for more samples or processing steps per experiment. This is particularly important when analyzing precious samples (e.g., pediatric samples, leukocytes isolated from biopsies, rare antigen-specific lymphocytes and mouse tissues that yield a small number of cells). Although it is currently possible to simultaneously measure up to 11 distinct fluorescent colors through a convoluted series of novel developments in flow cytometry hardware, software, and dye chemistry, the use of these advances has been severely limited by the lack of commercial availability of spectrally distinct directly labeled primary and secondary antibodies. Although labeled secondary antibodies directed at individual isotype-specific targeting antibodies (e.g., anti-IgG$_1$ isotype antibodies) exist, it is not possible to use this type of labeled antibody to detect more than one of the same isotype of an antibody (e.g., an IgG$_1$ isotype antibody) in a single sample due to cross-reactivity. The current invention overcomes these limitations by providing for a convenient and extremely versatile method of rapidly labeling either small or large quantities of any primary antibody including primary antibodies of the same isotype to be used in, for example, multicolor flow cytometry and on Western blots. This advance in multicolor systems has a number of advantages over current two- and three-color flow cytometric measurements. For example, no combination of one-color stains can accurately enumerate or be used to isolate CD3$^+$ CD4$^+$ CD8$^-$ T cells (excluding, for example CD3$^+$ CD4$^+$ CD8$^+$ T cells and small CD4$^+$ monocytes). The use of cell membrane markers to study leukocyte composition in blood and tissue serves as an example of an analytical monoclonal antibody application, particularly in combination with flow cytometry. It is also the example most relevant to studies of the immune system, because the cellular composition of blood and lymphoid tissue provides a 'window', allowing the analysis and monitoring of the immune system.

The methods of the invention can also be used in immunofluorescence histochemistry. This technique involves the use of antibodies labeled with fluorophores to detect substances within a specimen. The pathologist derives a great deal of information of diagnostic value by examining thin sections of tissue in the microscope. Tissue pathology is particularly relevant to, for example, the early diagnosis of cancer or premalignant states, and to the assessment of immunologically mediated disorders, including inflammation and transplant rejection. The problems associated with immunofluorescence histochemistry, however, stem from the limitations of the methods currently available for use in such application. For example, directly labeling an antibody can result in antibody inactivation and requires a relatively large of amount of antibody and time to do the conjugation. It is also expensive and impractical to prepare directly labeled antibodies having variable degrees of label substitution. Similarly, indirect labeling of an antibody has problems, such as lack of secondary antibody specificity, and reliance upon primary antibody differences, including antibody isotypes and available fluorophores, to do multicolor labeling. Secondary antibody labeling is not practical where the primary antibody is from the same species or of the same isotypes. Combinations of fluorophores or other detectable labels on the same target-binding antibody, which can be readily prepared in multiple mixtures by the methods on this invention, greatly increase the number of distinguishable signals in multicolor protocols. Lack of secondary antibody specificity arises when the specimen containing the targeted moiety and target-binding antibody are from homologous species. For example, BrdU-labeled DNA in rodent tissue is detected by immunohistochemical staining. The target-binding antibody is conventionally mouse anti-BrdU, and the detecting antibody system uses an anti-mouse immunoglobulin antibody, labeled with fluorescein. Because there is homology between mouse immunoglobulin and immunoglobulins from a number of rodent species (for example, rats, mice, hamsters, etc.), the detecting antibody not only binds to the target-binding antibody, but also nonspecifically binds to immunoglobulin in the tissue. The current invention eliminates this problem by pre-forming the immunolabeling complex and allows for a simple, rapid and convenient method to proceed with labeling with two, three or more fluorescent antibodies in one experiment. Very significantly, it can always be used with primary antibodies of either the same or different isotype, and always on tissue of the same or similar species as the primary antibody.

The instant invention also has application in the field of microarrays. Microarray technology is a powerful platform for biological exploration (Schena (Ed.), Microarray Biochip Technology, (2000)). Many current applications of arrays, also known as "biochips," can be used in functional genomics as scientists seek characteristic patterns of gene expression in different physiopathological states or tissues. A common method used in gene and protein microarray technology involves the use of biotin, digoxigenin (DIG), or dinitrophenyl (DNP) as an epitope or a "tag" such as an oligohistidine, glutathione transferase, hemagglutinin (HA), or c-myc. In this case a detectably labeled anti-biotin, anti-DIG, anti-DNP, anti-oligohistidine, anti-glutathione transferase, anti-HA, or anti-c-myc is used as the detection reagent. The instant invention allows for the use of multiple fluorophore- or enzyme-labeled antibodies, thereby greatly expanding the detection modalities and also providing for enhanced multiplexing and two-dimensional analysis capabilities.

Similarly, the invention can be used with protein microarrays and on Western blots. Protein microarrays can provide a practical means to characterize patterns of variation in hundreds of thousands of different proteins in clinical or research applications. Antibody arrays have been successfully employed that used a set of 115 antibody/antigen pairs for detection and quantitation of multiple proteins in complex mixtures (Haab et al., Genome Biology, 2, 4.1 (2001)). However, protein microarrays use very low sample volumes, which historically have significantly limited the use of antibody technology for this application. The invention of the application readily overcomes this limitation and provides a means to label antibodies with the fluorescent dyes using a very low sample volume and to automate formation of the staining complex and the staining process.

The present invention also provides a means for the specific detection, monitoring, and/or treatment of disease and contemplates the use of immunolabeling complexes to detect the presence of particular targets in vitro. In such immunoassays, the sample may be utilized in liquid phase, in a gel, or bound to a solid-phase carrier, such as an array of fluorophore-labeled microspheres (e.g., U.S. Pat. Nos. 5,981,180 and 5,736,330). For example, a sample can be attached to a polymer, such as aminodextran, in order to link the sample to an insoluble support such as a polymer-coated bead, plate, or tube. For instance, but not as a limitation, using the methods of the present invention in an in vitro assay, antibodies that specifically recognize an antigen of a particular disease are used to determine the presence and amounts of this antigen.

Likewise, the immunolabeling complexes of the present invention can be used to detect the presence of a particular target in tissue sections prepared from a histological specimen. Preferably, the tissue to be assayed will be obtained by surgical procedures, e.g., biopsy. The excised tissue will be assayed by procedures generally known in the art, e.g. immunohistochemistry, for the presence of a desired target that is recognized by an immunolabeling complex, as described above. The tissue may be fixed or frozen to permit histological sectioning. The immunolabeling complex may be labeled, for example with a dye or fluorescent label, chemical, heavy metal or radioactive marker to permit the detection and localization of the target-binding antibody in the assayed tissue. In situ detection can be accomplished by applying a detectable immunolabeling complex to the tissue sections. In situ detection can be used to determine the presence of a particular target and to determine the distribution of the target in the examined tissue. General techniques of in situ detection are well known to those of ordinary skill. See, for example, Ponder, "Cell Marking Techniques and Their Application," in MAMMALIAN DEVELOPMENT: A PRACTICAL APPROACH, Monk (ed.), 115 (1987).

For diagnosing and classifying disease types, tissues are probed with an immuno-labeled complex, as defined above, that comprises a target-binding antibody to a target antigen associated with the disease, e.g., by immunohistochemical methods. Where the disease antigen is present in body fluids, such immuno-labeled complexes comprising a target-binding antibody to the disease antigen are preferably used in immunoassays to detect a secreted disease antigen target.

Detection can be by a variety of methods including, for example, but not limited to, flow cytometry and diagnostic imaging. When using flow cytometry for the detection method, the use of microspheres, beads, or other particles as solid supports for antigen-antibody reactions in order to detect antigens or antibodies in serum and other body fluids is particularly attractive. Flow cytometers have the capacity to detect particle size and light scattering differences and are highly sensitive fluorescence detectors. Microfluidic devices provide a means to perform flow-based analyses on very small samples.

Alternatively, one can use diagnostic imaging. The method of diagnostic imaging with radiolabeled antibodies is well known. See, for example, Srivastava (ed.), RADIOLABELED MONOCLONAL ANTIBODIES FOR IMAGING AND THERAPY, Plenum Press (1988); Chase, "Medical Applications of Radioisotopes," in REMINGTON'S PHARMACEUTICAL SCIENCES, 18$^{th}$ Edition, Gennaro et al. (eds.) Mack Publishing Co., 624 (1990); and Brown, "Clinical Use of Monoclonal Antibodies," in BIOTECHNOLOGY AND PHARMACY, Pezzuto et al. (eds.), Chapman & Hall, 227 (1993). This technique, also known as immunoscintigraphy, uses a gamma camera to detect the location of gamma-emitting radioisotopes conjugated to antibodies. Diagnostic imaging is used, in particular, to diagnose cardiovascular disease and infectious disease.

Thus, the present invention contemplates the use of immuno-labeled complexes to diagnose cardiovascular disease. For example, immuno-labeled complexes comprising anti-myosin antibodies can be used for imaging myocardial necrosis associated with acute myocardial infarction. Immuno-labeled complexes comprising antibodies that bind platelets and fibrin can be used for imaging deep-vein thrombosis. Moreover, immuno-labeled complexes comprising antibodies that bind to activated platelets can be used for imaging atherosclerotic plaque.

Immuno-labeled complexes of the present invention also can be used in the diagnosis of infectious diseases. For example, immuno-labeled complexes comprising antibodies that bind specific bacterial antigens can be used to localize abscesses. In addition, immuno-labeled complexes comprising antibodies that bind granulocytes and inflammatory leukocytes can be used to localize sites of bacterial infection. Similarly, the immuno-labeled complexes of the present invention can be used to detect signal transduction in cells, the products of signal transduction, and defects, inhibitors, and activators of signal transduction.

Numerous studies have evaluated the use of antibodies for scintigraphic detection of cancer. Investigations have covered the major types of solid tumors such as melanoma, colorectal carcinoma, ovarian carcinoma, breast carcinoma, sarcoma, and lung carcinoma. Thus, the present invention contemplates the detection of cancer using immuno-labeled complexes comprising antibodies that bind tumor markers (targets) to detect cancer. Examples of such tumor markers include carcinoembryonic antigen, α-fetoprotein, oncogene products, tumor-associated cell surface antigens, and necrosis-associated intracellular antigens. In addition to diagnosis, antibody imaging can be used to monitor therapeutic responses, detect recurrences of a disease, and guide subsequent clinical decisions and surgical procedures. In vivo diagnostic imaging using fluorescent complexes that absorb and emit light in the near infrared (such as those of the Alexa Fluor 700 and Alexa Fluor 750 dyes) is also known.

EXAMPLES

The following examples describe specific aspects of the invention to illustrate the invention and to provide a description of the methods for those of skill in the art. The examples should not be construed as limiting the invention, as the examples merely provide specific methodology useful in understanding and practicing the invention.

Example 1

Preparation of Fc Antigen

Purified mouse and rabbit IgG was fragmented with the proteolytic enzyme papain (CURRENT PROTOCOLS IN CELL BIOLOGY, 16.4.1-16.4.10 (2000)). A 12 mL solution of mouse IgG was prepared at ~2 mg/mL in phosphate-buffered saline (PBS). A solution containing 0.1 mg of papain in digestion buffer (PBS, 0.02 M EDTA, 0.02 M cysteine) was added to the antibody and allowed to react at 37° C. for 16 hours. The digestion was terminated by the addition 20 μL of 0.3 M iodoacetamide in PBS. The fragments were dialyzed against 2 L of PBS for 16 hours at 4° C. The Fc fragment was purified on a protein G-Sepharose CL-4B column. The bound fraction containing the Fc fragment was eluted from the column using 50-100 mM glycine/HCl buffer, pH 2.5-2.8. The eluate was collected in 1 mL fractions. The pH of the protein fractions was immediately raised to neutral by addition of 100 μL of either 500 mM phosphate or Tris buffer, pH 7.6, to each 1 mL fraction. The solution was then loaded onto a Sephacryl S-200 Superfine size-exclusion column and fractions corresponding to a molecular weight of ~50 kDa were collected and analyzed by SDS-PAGE and HPLC.

Example 2

Production of Anti-Fc Antibodies

Polyclonal antibodies specific for the Fc region of an antibody were raised in goats against the purified FC region of an antibody from a different species (Example 1). Methods of immunizing animals are well known in the art, and suitable immunization protocols and immunogen concentrations can be readily determined by those skilled in the art (Current Protocols in Immunology 2.4.1-9 (1995); ILAR Journal 37, 93 (1995)). Briefly, individual goats were immunized with purified mouse Fc or purified rabbit Fc fragments. The initial immunization in 50% Freund's complete adjuvant (1000 μg conjugate (half subcutaneous, half intramuscularly)) was followed by 500 μg conjugate per goat in Freund's incomplete adjuvant two and four weeks later and at monthly intervals thereafter. Antibodies were purified from serum using protein A-Sepharose chromatography. Antibodies against mouse Fc isotypes can be prepared by starting with isotype-selected mouse Fc antigens. Rabbits have a single Fc isotype. Characterization of the selectivity and cross-reactivity of isotype-specific antibodies is by standard techniques, including HPLC.

Example 3

Preparation of Fab Fragments

Fragmentation of the goat anti-(mouse Fc) antibody to the monovalent Fab fragment was carried out using the proteolytic enzyme, papain, as described in Example 1. Following dialysis against PBS, the Fab fragment was purified on a protein A-Sepharose CL-4B column. The unbound fraction containing the Fab fragment and the papain was collected. This solution was then loaded onto a Sephacryl S-200 Superfine size-exclusion column and fractions corresponding to a molecular weight of ~50 kDa were collected and analyzed by SDS-PAGE. The Fab fragments of goat anti-(rabbit Fc) can be prepared similarly.

Example 4

Preparation of the Labeled Antibody Immunoglobulin-Binding Protein or the Non-Antibody Immunoglobulin-Binding Peptide and Protein Conjugates in Homogeneous Solution Conjugates of antibody immunoglobulin-binding protein or the non-antibody immunoglobulin-binding peptides or proteins with low molecular weight dyes and haptens such as biotin or digoxigenin are typically prepared from succinimidyl esters of the dye or hapten, although reactive dyes and haptens having other protein-reactive functional groups are also suitable. The typical method for protein conjugation with succinimidyl esters is as follows. Variations in molar ratios of dye-to-protein, protein concentration, time, temperature, buffer composition and other variables that are well known in the art are possible that still yield useful conjugates.

A protein solution of the Fab fragment of goat anti-(rabbit Fc), goat anti-(mouse Fc), protein A, protein G, or protein L or an immunoglobulin-binding peptide (e.g., a peptide identified by screening a library of peptides) is prepared at ~10 mg/mL in 0.1 M sodium bicarbonate (pH ~8.3). The labeling reagents are dissolved in a suitable solvent such as DMF at ~10 mg/mL. Predetermined amounts of the labeling reagents are added to the protein solution with stirring. A molar ratio of 10 moles of dye to 1 mole of protein is typical, though the optimal amount can be varied with the particular labeling reagent, the protein being labeled and the protein's concentration. The optimal ratio was determined empirically. When optimizing the fluorescence yield and determining the effect of degree of substitution (DOS) on the conjugate's brightness, it is typical to vary the ratio of reactive dye to protein over a several-fold range. The reaction mixture is incubated at room temperature for a period that is typically one hour or on ice for several hours. The dye-protein conjugate is typically separated from unreacted reagents by size-exclusion chromatography, such as on BIO-RAD P-30 resin equilibrated with PBS. The initial, protein-containing band is collected and the DOS is determined from the absorbance at the absorbance maximum of each fluorophore, using the extinction coefficient of the free fluorophore. The DOS of nonchromophoric labels, such as biotin, is determined as described in Haugland (Haugland et al., Meth. Mol. Biol. 45, 205 (1995); Haugland, Meth. Mol. Biol. 45, 223 (1995); Haugland, Meth. Mol. Biol. 45, 235 (1995); Haugland, Current Protocols in Cell Biol. 16.5.1-16.5.22 (2000)). Using the above procedures, conjugates of goat anti-(mouse Fc) and goat anti-(rabbit Fc) were prepared with several different Alexa Fluor dyes, with Oregon Green dyes, with biotin-X succinimidyl ester, with desthiobiotin-X succinimidyl ester, with succinimidyl 3-(2-pyridyldithio)propionate (SPDP) and with succinimidyl trans-4-(maleimidylmethyl)cyclohexane-1-carboxylate (SMCC).

Some dye conjugates of protein A and protein G, including those of some Alexa Fluor dyes, are commercially available, such as from Molecular Probes. Inc. (Eugene, Oreg.). The interspecies specificity and approximate affinity of some other non-antibody immunoglobulin-binding proteins bind to segments of a target antibody, such as that of protein A and protein G are known (Langone, Adv. Immunol. 32, 157 (1982); Surolia et al., Trends Biochem. Sci. 7, 74 (1982); Notani et al., J. Histochem. Cytochem. 27, 1438 (1979); Goding, J. Immunol. Meth. 20, 241 (1978); J. Immunol. Meth. 127, 215 (1990); Bjorck et al., J. Immunol. 133, 969 (1984)).

In addition, labeling proteins (goat Fab anti-(mouse Fc), goat Fab anti-(mouse lambda light chain), goat Fab anti-(mouse kappa light chain), protein A, protein G, protein L, lectins, single-chain fragment variable antibodies (ScFv)) conjugated to the detectable labels of R-phycoerythrin (R-PE), allophycocyanin (APC), tandem conjugates of phycobiliproteins with chemical dyes including several Alexa Fluor dyes, horseradish peroxidase (HRP), *Coprinus cinereus* peroxidase, *Arthromyces ramosus* peroxidase, glucose oxidase and alkaline phosphatase (AP) were or can be prepared by standard means (Haugland et al., Meth. Mol. Biol. 45, 205 (1995); Haugland, Meth. Mol. Biol. 45, 223 (1995); Haugland, Meth. Mol. Biol. 45, 235 (1995); Haugland, Current Protocols in Cell Biol 16.5.1-16.5.22 (2000)). Fusion proteins, such as of protein G or protein A with detectable labels such as luciferin, aequorin, green-fluorescent protein and alkaline phosphatase are also known that are suitable for practice of the invention (Sun et al., J. Immunol. Meth. 152, 43 (1992); Eliasson et al., J. Biol. Chem. 263, 4323 (1988); Eliasson et al., J. Immunol. 142, 575 (1989)).

Immunoglobulin heavy and light chains, like most secreted and membrane bound proteins, are synthesized on membrane-bound ribosomes in the rough endoplasmic endoplasmic reticulum where N-linked glycosylation occurs. The specificity of lectins for carbohydrates, including N-linked glycoproteins, is also known (EY laboratories, Inc. Lectin Conjugates Catalog, 1998).

Example 5

Preparation of the Labeled Antibody Immunoglobulin-Binding Protein or the Non-Antibody Immunoglobulin-Binding Peptide and Protein Conjugates while Bound to an Affinity Matrix Unlabeled Fab fragment for goat anti-(mouse Fc) (prepared as in Example 3) was bound to agarose-immobilized mouse IgG for one hour. Following a wash step with bicarbonate buffer, pH 8.3, the complex of immobilized IgG and unlabeled Fab was labeled for one hour at room temperature with the succinimidyl ester of the amine-reactive label. Unconjugated dye was eluted with bicarbonate buffer, and then the covalently labeled Fab fragment was eluted with 50-100 mM glycine/HCl buffer, pH 2.5-2.8. The eluate was collected in 1 mL fractions. The pH of the protein fractions was immediately raised to neutral by addition of 100 µL of either 500 mM phosphate or Tris buffer, pH 7.6, to each 1 mL fraction. Variations of the reagent concentrations, labeling times, buffer composition, elution methods and other variables are possible that can yield equivalent results. Conjugates of the Fab fragment of goat anti-(rabbit Fc) and of protein G and protein A are prepared similarly.

Example 6

Comparison of the Alexa Fluor 488 Dye-Labeled Fab Fragments of Goat Anti-(Mouse Fc) Prepared as in Example 4 and as in Example 5

Conjugates of the Fab fragment of goat anti-(mouse Fc) with the Alexa Fluor 488 succinimidyl ester were separately prepared, as described in Examples 4 and 5. The conjugates had estimated degrees of substitution of ~1.9 (labeled as in Example 4) and ~3.0 (labeled as in Example 5), respectively, and virtually identical absorption and emission spectral maxima. When excited at 488 nm, conjugates prepared using the fragment prepared as described in Example 5 were about 3.2-times more fluorescent than using the fragments that were prepared in Example 4 (FIG. 8) as detected by flow cytometry when bound to CD3 on Jurkat T cells. Similar results were observed with other dyes.

Example 7

Preparation of a Labeling Protein from Protein G and Albumins

Native protein G has a high affinity binding (nanomolar) site for albumins, in particular ovalbumin. Equal weights of protein G and Texas Red ovalbumin (Molecular Probes. Inc.) were dissolved in PBS, pH 7.5. After one hour, the resulting complex was separated on a Sephacryl S-200 Superfine size-exclusion column and analyzed by SDS-PAGE and HPLC. Alternatively, the protein G is combined with a labeled albumin while the protein G is immobilized on any of the several immunoglobulins to which it binds, and the excess labeled albumin is washed away preceding elution of the albumin-labeled protein G complex from the matrix.

Example 8

Preparation of an Immunolabeling Complex on a Very Small Scale

Submicrogram quantities of a target-binding antibody were complexed with submicrograms of a labeling protein in varying molar ratios of between about 1:1 and 1:20 to prepare an immunolabeling complex that was suitable for staining a sample. For instance, 0.1 µg of mouse monoclonal anti-α-tubulin in 1 µL PBS with 0.1% BSA was complexed with 0.5 µg of the Alexa Fluor 488 dye-labeled Fab fragment of goat anti-(mouse Fc) (prepared as in Example 4) or with 0.1 µg of the Alexa Fluor 488 dye-labeled Fab fragment of goat anti-(mouse Fc) (prepared as in Example 5) in 5 µL of PBS for 10 minutes at room temperature. The immunolabeling complex can be used immediately for staining tubulin in fixed-cell preparations (Example 16) or any excess unbound Alexa Fluor 488 dye-labeled Fab fragment of goat anti-(mouse Fc) in the immunolabeling complex can be captured with non-immune mouse IgG (Example 9) for combination with other antibody conjugates, including those of targeting antibodies that have been directly conjugated to other labels. Rabbit antibodies were labeled similarly using labeled goat anti-(rabbit Fc). Labeling of targeting antibodies with a labeled protein A, protein L, protein G, protein G complexed with a labeled albumin, or other immunoglobulin-binding peptides or proteins proceeds similarly. In the case of a mouse (or rat) monoclonal antibody, it is preferred to use a labeled protein that is selective for the specific isotype of the primary antibody (e.g. anti-(mouse $IgG_1$) for a mouse $IgG_1$ isotype primary antibody). Although some cross-reactivity for other mouse (or rat) isotypes was observed using a goat antibody that was selective for mouse $IgG_1$ isotype monoclonal antibodies, routine and optimal use for labeling unmatched mouse isotypes required greater amounts of immunolabeling complexes and was somewhat less reliable.

Example 9

Capturing Excess Immunoglobulin-Binding Protein by a Capturing Component

Figure 2:
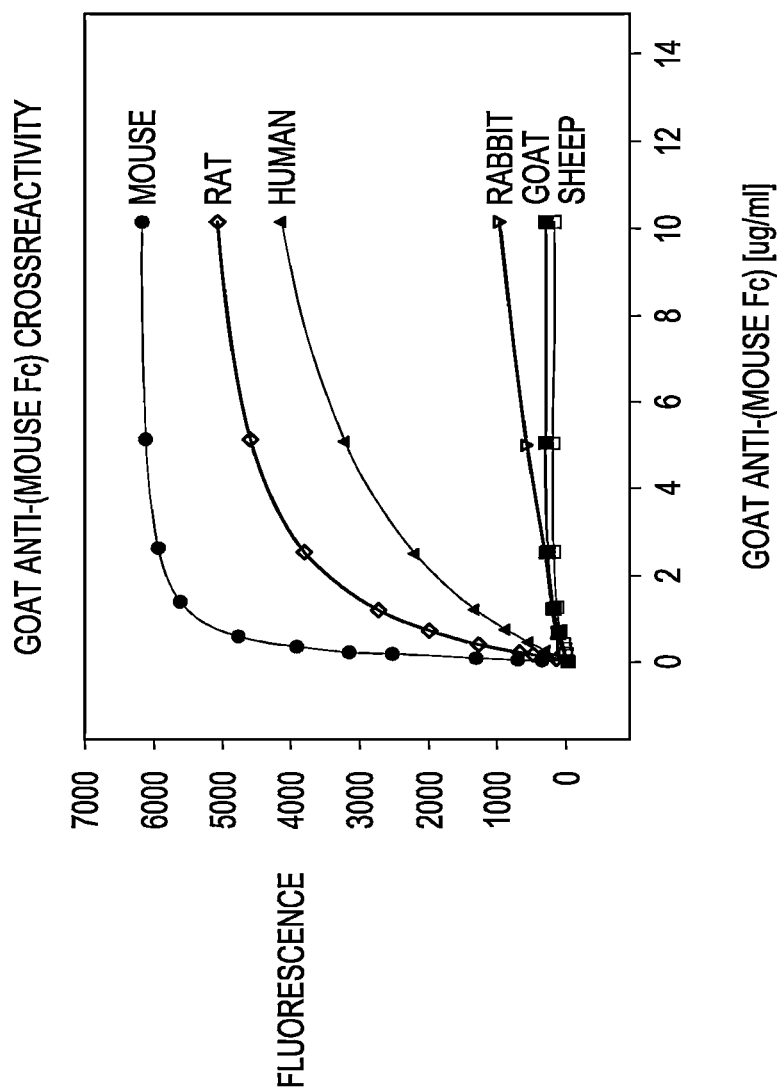
FIG. 2: Shows species specificity of goat Fab anti-(mouse Fc), as observed using a microplate coated with IgG of various species. The various species were blocked with BSA, reacted with biotinylated goat Fab anti-(mouse Fc), washed, and then treated with streptavidin-horseradish peroxidase (HRP), followed by hydrogen peroxide ($H_2O_2$) and the Amplex Red peroxidase detection reagent.

Immunolabeling complexes were prepared as described in Example 8. To the immunolabeling complex was added to each tube 25 µL of a 14.1 mg/mL stock solution of unlabeled mouse IgG to capture excess immunolabeling complexes. As shown in FIG. 1, not all of the immunoglobulin-binding protein was necessarily complexed with the target-binding antibody to form an immunolabeling complex. Consequently, particularly for applications in which labeling complexes of multiple primary antibodies from the same species (e.g. mouse monoclonal antibodies) or crossreacting species (e.g. mouse and human antibodies, FIG. 2, Table 1) were to be used simultaneously or sequentially, it is necessary to quench or otherwise remove any excess immunoglobulin-binding protein by use of a capturing component or by other means to avoid inappropriate labeling of the sample. The most effective capturing component to capture excess immunoglobulin-binding protein is one that contains the binding site of the targeting agent. For instance, whole mouse IgG or mouse serum was shown to be an effective and inexpensive reagent when the immunoglobulin-binding protein was bound to a segment of a mouse monoclonal antibody. The mouse IgG was added in excess to the amount of immunoglobulin-binding protein and incubated for a period of approximately 1-5 minutes, or longer.

It is preferred to prepare the immunolabeling complex and then add the capturing component shortly before the experiment. The rapid quenching effect permits this to be done within minutes of performing labeling of the sample by the immunolabeling complex. If desired, the excess capturing component can be removed following labeling of the sample by a simple wash step. Alternatively, fixation of the stained sample by aldehyde-based fixatives or other reagents or methods subsequent to incubation with the immunolabeling complex can provide permanent immobilization of the immunolabeling complex on its target in the sample. As an alternative to adding a soluble capturing component to the immunolabeling complex, the capturing component can be immobilized on an insoluble matrix such as agarose and the immunolabeling complex contacted with that matrix. A preferred matrix when labeling mouse antibodies to mouse antigens is mouse IgG immobilized on agarose. Excess labeled anti-rabbit antibodies can be captured using rabbit IgG that is free in solution or immobilized. Alternatively, the immunolabeling complex can be separated from any capturing component by chromatographic or electrophoretic means.

Example 10

HPLC Analysis of a Labeling Complex

Figure 6:
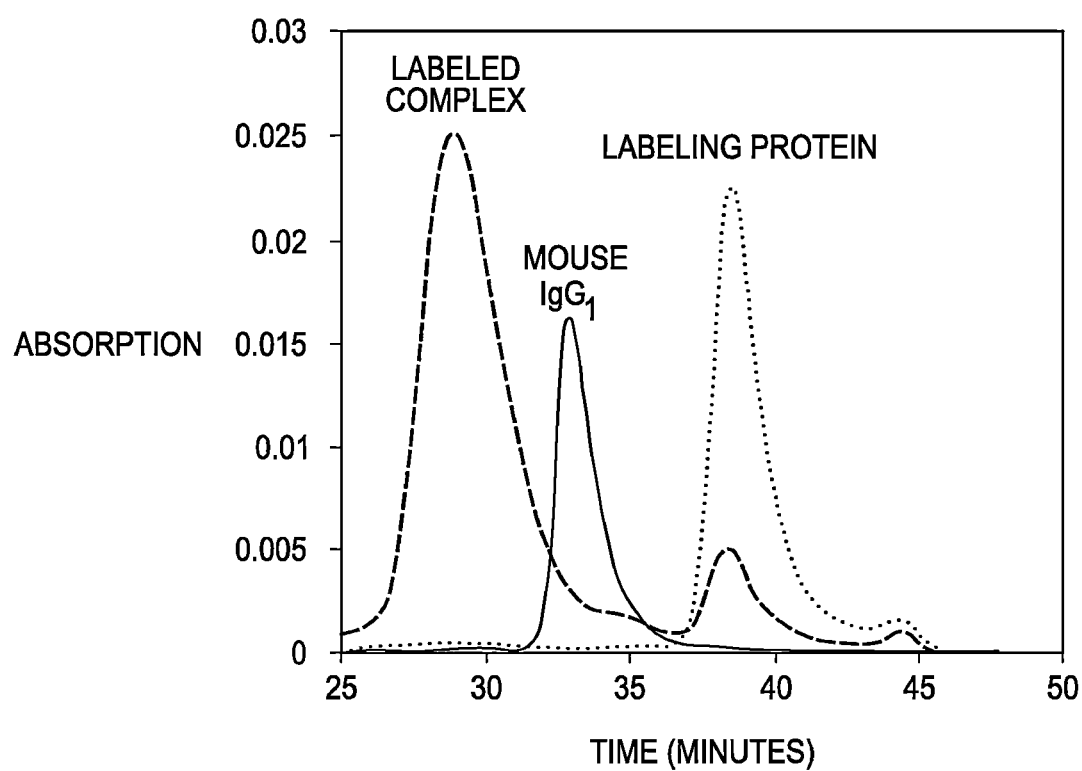
FIG. 6: Shows high-performance size-exclusion chromatographic analysis of Alexa Fluor 488 dye-labeled goat Fab anti-(mouse Fc) labeling reagent binding to a mouse $IgG_1$ target-binding antibody. The labeling reagent, alone, appears as a peak at 38 minutes; the target-binding antibody, alone, appears as a peak at 33 minutes. When labeling reagent and target-binding antibody are mixed together at a molar ratio of ~5:1 (labeling reagent:target-binding antibody), the resulting immunolabeling complex appears as a peak at 29 minutes (Example 10).
Figure 7:
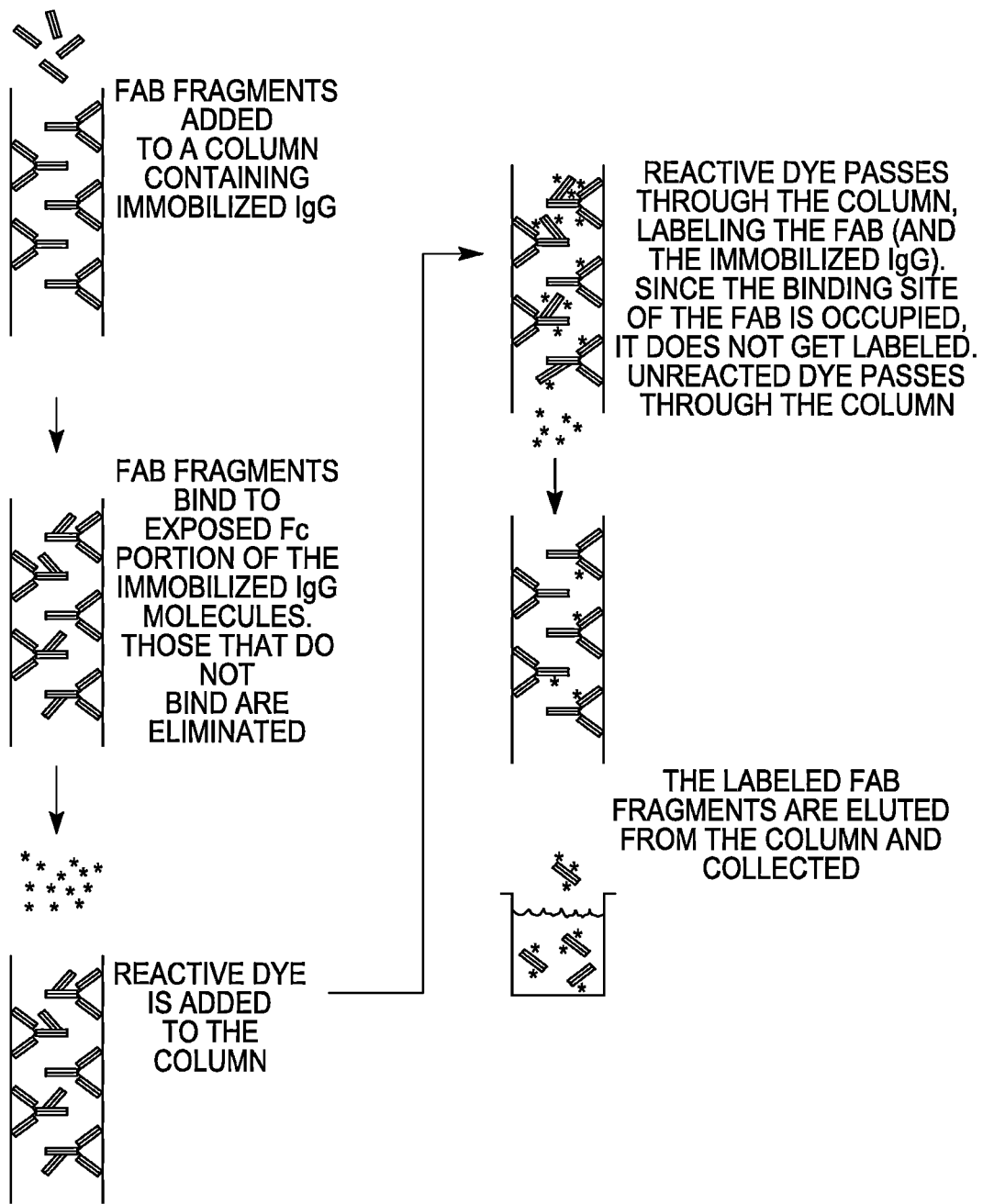
FIG. 7: Shows the production of labeling reagent wherein the label is attached to the labeling reagent when immobilized on a column.

In order to analyze the success and extent of complex formation of the labeling protein with the target-binding antibody, size exclusion HPLC of the samples was performed. For instance, a complex of Alexa Fluor 488 dye-labeled goat Fab anti-(mouse Fc) with a monoclonal mouse anti-tubulin in molar ratios of approximately 1:1, 3:1, 5:1 and 10:1. These were separated by analytical HPLC using a BioSep S-3000 column and eluting with 0.1 M NaP$_i$, 0.1 M NaCl, pH 6.8, at a flow rate of 0.25 mLs/min. An example of the separation using the 5:1 molar ratio (FIG. 6) demonstrates that, using this molar ratio, formation of the labeled complex is essentially quantitative.

Example 11

Cross-Reactivity of Goat Fab Anti-(Mouse Fc) to Other Species of IgG

Microplates were equilibrated overnight with IgG from a mouse or non-mouse species, and then further blocked with BSA. Variable amounts of the biotinylated Fab fragment of goat anti-(mouse Fc) were added to each well and allowed to bind. After washing, streptavidin-HRP and the Amplex Red peroxidase substrate were added. HRP activity was detected by the addition of $H_2O_2$ using the Amplex Red Peroxidase Assay Kit (Molecular Probes, Inc., Eugene, Oreg.). Reactions containing 200 µM Amplex Red reagent, 1 U/mL HRP and 1 mM $H_2O_2$ (3% solution) in 50 mM sodium phosphate buffer, pH 7.4, were incubated for 30 minutes at room temperature. Fluorescence was measured with a fluorescence microplate reader using excitation at 560±10 nm and fluorescence detection at 590±10 nm. Background fluorescence, determined for a no-$H_2O_2$ control reaction, was subtracted from each value (Table 1 and FIG. 2). Table 1 shows that the goat anti-(mouse Fc) antibody because of the highly conserved structure of the Fc region of an antibody it can be used to complex other non-mouse antibodies, including rat, and human antibodies. The goat anti-mouse IgG antibody reaction with mouse antibody was set at 100% and the crossreacting antibodies were expressed as a percentage compared the mouse on mouse data. The data in Table 1 show that the Fab fragment of the goat anti-(mouse Fc) antibody of the current invention does not strongly bind to the goat or sheep Fc domain; however, one skilled in the art could generate antibodies that will react with the goat and sheep Fc domain or the Fc domain of any other species. Biotinylated Fab goat anti-(mouse Fc) was used in this example because it provided a convenient method to quantitate the amount of crossreactivity in a conventional method but it could have been accomplished using a fluorophore Fab labeled goat anti-(mouse Fc). It was demonstrated by HPLC (as in Example 10) that Alexa Fluor 488 dye-labeled goat anti-(rabbit Fc) bound to rabbit primary antibodies.

TABLE 1

Cross-reactivity of goat anti-mouse IgG antibody with other non-mouse antibodies.

| Species | Crossreactivity | % Fluorescence |
| --- | --- | --- |
| Mouse | ++++ | 100 |
| Rat | +++ | 80.7 |
| Human | ++ | 66.7 |
| Rabbit | + | 16.9 |
| Goat | − | 6.5 |
| Sheep | − | 5.7 |

Example 12

Figure 3:
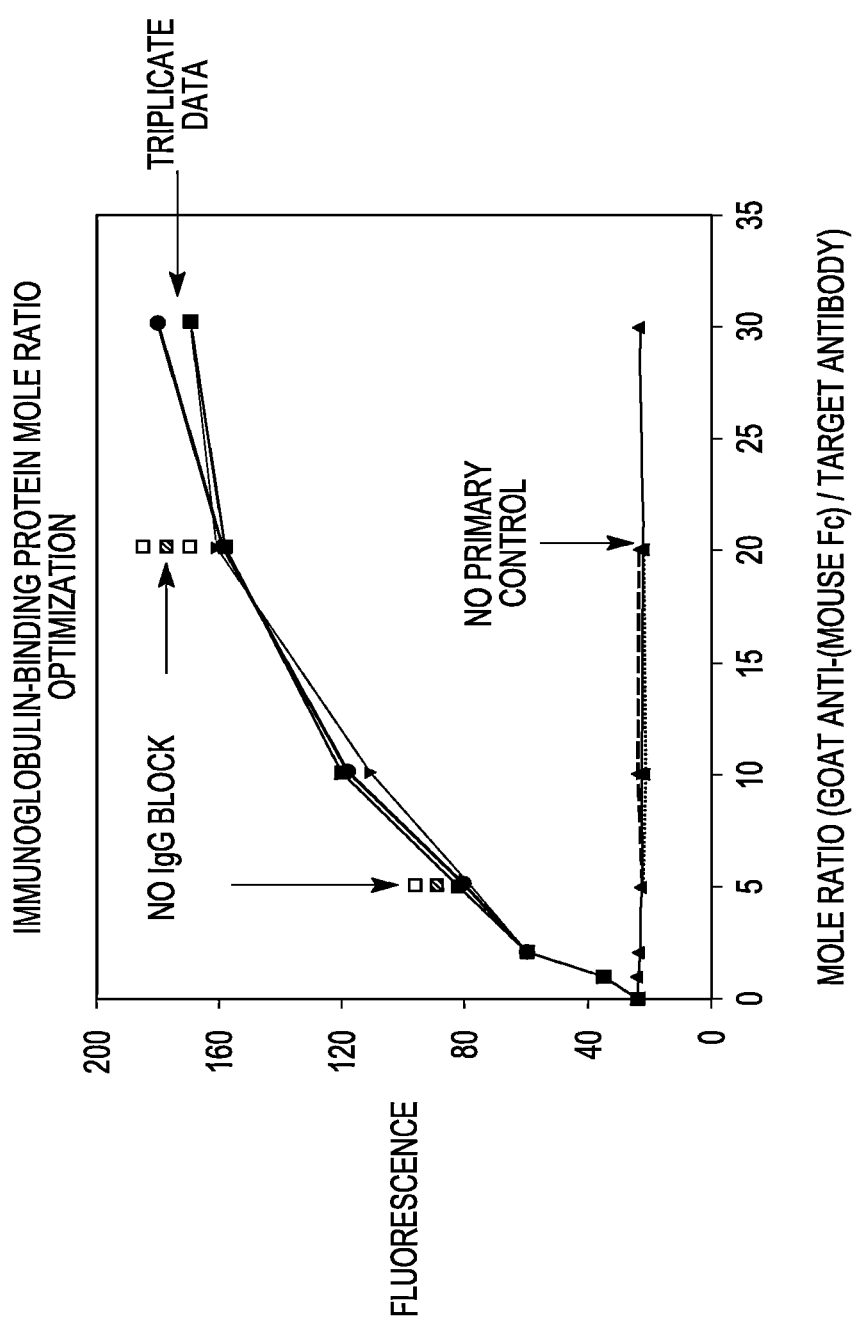
FIG. 3: Shows a preferred molar ratio of a goat Fab anti-(mouse Fc) labeling reagent. Varying amounts of an Alexa Fluor 488 dye-labeled Fab fragment of goat anti-(mouse Fc) were added to a constant amount of anti-biotin monoclonal antibody (mAb). This mixture was equilibrated for 20 minutes, and then added to biotinylated-BSA in a microplate well. After allowing time to bind, the plates were washed and the remaining fluorescence was quantitated. The analysis was performed in triplicate (circles). Control experiments were performed, as described above, but without adding the primary anti-biotin antibody (solid squares).
Figure 4:
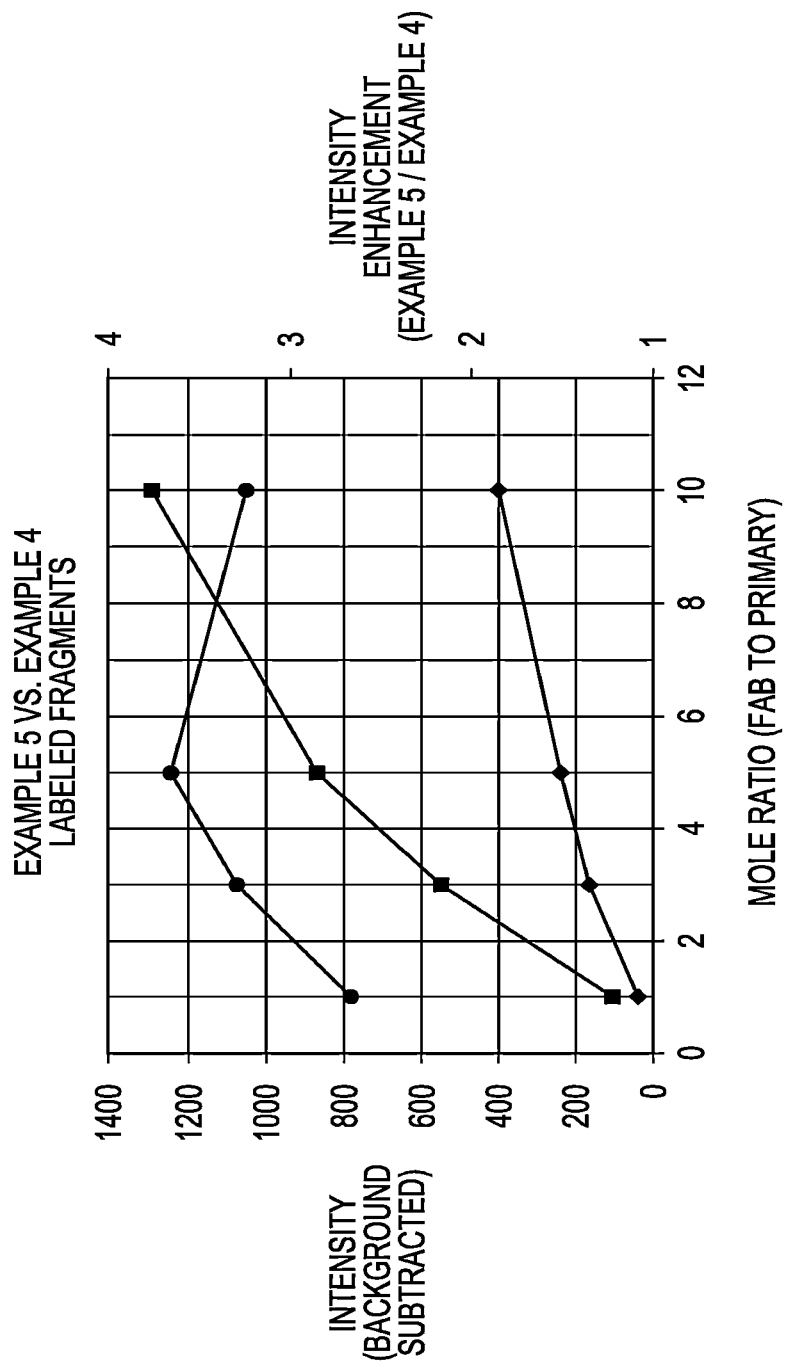
FIG. 4: Shows a comparison of the fluorescence intensity (Example 6) for labeling reagent prepared in homogeneous solution (Example 4) and labeling reagent prepared on a column (Example 5).

Determination of the Optimal Molar Ratio of Immunoglobulin-Binding Protein to Target Antibody Using a Microplate Assay To 1.6 µg of mouse monoclonal anti-biotin (MW ~145,000) in 8.0 µL PBS was added varying amounts of the Alexa Fluor 488 dye-labeled Fab fragment of goat anti-(mouse Fc) (MW ~50,000) (prepared as in Example 4) to form an immunolabeling complex. After equilibration for 20 min, a 100 µL aliquot was added to a 96-well microplate coated with biotinylated BSA. After 30 minutes, the plates were washed and the residual fluorescence was quantitated using a fluorescence microplate reader using excitation at 485+/−10 nm and detecting emission at 530+/−12.5 nm. As shown in FIG. 3, a molar ratio of the Alexa Fluor 488 dye-labeled Fab fragment of goat anti-(mouse Fc) to the anti-biotin between 5 to 20 was sufficient to form appreciably detectable complexes (FIG. 3; fluorescence quantitated, performed in triplicate (circles); control experiments performed but without adding the primary anti-biotin antibody (solid squares)). A molar ratio of about 5 to about 10 was preferred for this pair of immunoglobulin-binding protein and target antibody. This ratio can be varied somewhat to increase or decrease the signal or to affect the consumption of valuable reagents. The weight ratio of immunoglobulin-binding protein to target-binding antibody is particularly affected by the actual molecular weight of the immunoglobulin-binding protein.

For instance, equal weights of the dye-labeled goat Fab anti-(mouse Fc) (prepared as in Example 5) and an intact mouse primary antibody, which corresponds to an approximately 3 to 1 molar ratio, usually yields suitable labeling complexes. Fluorescence intensity (or enzymatic activity) of the immunolabeling complex is readily adjusted by a corresponding adjustment of the amount of labeled Fab fragment used.

Similar analyses of the ratio for other labeling proteins (including those of labeled protein A, protein G, protein L, IgG-binding peptides and antibodies to other segments of the primary antibody), and for conjugates of labels other than Alexa Fluor 488 dye (including enzymes in combination with the appropriate enzyme substrates) are done essentially as described in this example.

Example 13

Dissociation Rate of the Immunolabeling Complex

A pre-equilibrated immunolabeling complex was prepared from 50 µg of an Alexa Fluor 488 dye-labeled Fab fragment of goat anti-(mouse Fc) and 15 µg of an anti-biotin monoclonal antibody (mAb). The immunolabeling complex was rapidly diluted with capturing component sufficient to give a 6.2 molar excess over the anti-biotin mAb. At various times, an aliquot was taken and added to a microplate well containing an excess of biotinylated BSA. After 30 minutes, the plates were washed and the remaining fluorescence was quantitated. Displacement of the labeling protein from the target-binding antibody through exchange was measured by any time-dependent decrease in fluorescence in the microplate well. For example the fragments prepared as described in Example 4 had 68 percent fragments bound to the target-binding antibody after 30 minutes compared to 87 percent of bound fragments that were prepared according to Example 5. One hour showed a similar decrease, 56 percent and 68 percent respectively. The labeling protein was shown to undergo a stable interaction with the target-binding antibody, with a lifetime for half exchange under these conditions of 3.5 hours. Dissociation rates were measured for labeling protein prepared according to Example 4 and for labeling protein prepared according to Example 5, demonstrating the greater stability of immunolabeling complexes made using the labeling proteins prepared according to Example 5.

Example 14

Protocol for Staining Cultured Cells with a Single Immunolabeling Complex

Culturable cells, such as bovine pulmonary artery endothelial cells (BPAEC), were grown on a 22×22 mm glass coverslip. The cells were fixed for 10 minutes using 3.7% formaldehyde in DMEM with fetal calf serum (FCS) at 37° C. The fixed cells were washed 3 times with PBS. The cells were permeabilized for 10 min with 0.02% Triton X-100 in PBS, washed 3× with PBS and blocked for 30 min with 1% BSA in PBS. Variations of the cell type and cell preparation, fixation, and permeabilization methods, including methods for antigen retrieval, are well known to scientists familiar with the art. An immunolabeling complex was prepared as described in Example 8. The immunolabeling complex was added directly to the fixed and permeabilized cells in an amount sufficient to give a detectable signal if there is a binding site for the primary antibody present in the sample. After an incubation period that was typically 10-60 minutes (usually about 15-30 minutes), the cells were washed with fresh medium and the labeling was evaluated by methods suitable for detection of the label. Staining by the immunolabeling complex can be additionally preceded, followed by or combined with staining by additional reagents, such as DAPI, which yields blue-fluorescent nuclei.

Example 15

Protocol for Staining Cultured Cells with Multiple Immunolabeling Complexes

Cells were fixed and permeabilized as described in Example 14. Multiple immunolabeling complexes were individually prepared from a variety of labeling proteins, according to the procedure described in Example 8. The multiple immunolabeling complexes were either used individually or sequentially to stain the cells, according to the procedure described in Example 14, or two or more immunolabeling complexes were formed then co-mixed in a single staining solution and used to simultaneously stain the sample. The optimal method for cell fixation and permeabilization and the best ratio for combination of the immunolabeling complexes are typically determined by preliminary experimentation using single immunolabeling complexes or multiple immunolabeling complexes used in combination. A first immunolabeling complex was prepared from an Alexa Fluor 488 dye-labeled Fab fragment of goat anti-(mouse Fc) and mouse monoclonal anti-α-tubulin, a second immunolabeling complex was prepared from an Alexa Fluor 568 dye-labeled Fab fragment of goat anti-(mouse Fc) and mouse monoclonal anti-vimentin (anti-vimentin was an ascites fluid preparation) and a third immunolabeling complex was prepared from an Alexa Fluor 647 dye-labeled Fab fragment of goat anti-(mouse Fc) and mouse monoclonal anti-cdc6 peptide antibody (Molecular Probes). Aliquots of the three different immunolabeling complexes were combined and used to stain BPAE cells for 30 minutes, washed with fresh medium and observed by fluorescence microscopy using optical filters appropriate for the three dyes. In this example, some cells showed cytoplasmicq staining by the anti-vimentin antibody, nuclear staining by the anti-cdc6 peptide antibody and staining of mitotic spindles by the anti-α-tubulin antibody, indicative of a cell in mitosis. Staining by the immunolabeling complexes was additionally preceded, followed by or combined with staining by additional reagents, such as Alexa Fluor 350 phalloidin, which yielded blue-fluorescent actin filaments in the above example.

The immunolabeling complexes that are used in combination do not have to be targeted toward antibodies from the same species. For instance, complexes of Alexa Fluor 488 dye-labeled goat anti-(mouse $IgG_1$ Fc) with a mouse $IgG_1$ monoclonal target-binding antibody and an Alexa Fluor 594 dye-labeled goat anti-(rabbit Fc) with a rabbit primary target-binding antibody can be prepared and used in combined staining protocols.

Example 16

Protocol for Staining Tissue with a Single Immunolabeling Complex

A mouse intestine cryosection (University of Oregon histology core facility), a cross-section of about 16 μm thickness, was mounted on a slide. The intestine was perfused and fixed with 4% formaldehyde prior to dissection, embedding, and sectioning. The tissue section was rehydrated for 20 minutes in PBS. An immunolabeling complex was prepared as described in Example 8. Briefly, 0.1 μg of mouse monoclonal anti-cdc6 peptide (a nuclear antigen) in 1 μL PBS with 0.1% BSA was complexed with 0.5 μg of the Alexa Fluor 350 dye-labeled Fab fragment of goat anti-(mouse $IgG_1$ Fc) (prepared as in Example 4) in 5 μL of PBS for 10 minutes at room temperature. Excess Fab fragment of goat anti-(mouse $IgG_1$ Fc) was captured with 25 μL of a 14.1 mg/mL stock of unlabeled mouse IgG. The tissue was permeabilized with 0.1% Triton X-100 for 10 min. The tissue was washed two times with PBS and was blocked in 1% BSA for 30 min. The immunolabeling complex was added directly to the tissue for 30 minutes and washed three times in PBS. The sample was mounted in Molecular Probes' Prolong antifade mounting medium and observed by fluorescence microscopy using optical filters appropriate for the Alexa Fluor 350 dye. Results showed that the mouse monoclonal anti-cdc6 peptide immunolabeling complex showed specific nuclear labeling in the mouse intestine tissue section. Variations of the tissue type and tissue preparation, fixation and permeabilization methods, mounting methods, including methods for antigen retrieval, are well known to scientists familiar with the art.

Example 17

Staining of a Tissue Target in Combination with Tyramide Signal Amplification (TSA)

Mouse brain cryosections were labeled with a pre-formed complex of horseradish peroxidase (HRP)-labeled goat anti-(mouse $IgG_1$ Fc) antibody and a mouse $IgG_1$ monoclonal anti-(glial fibrillary acidic protein (GFAP)) prepared essentially as in Example 8 using a molar ratio of labeling protein to monoclonal antibody of 3. Staining of the mouse tissues was essentially as in Example 16. The staining localization and intensity was compared to that of (a) goat anti-mouse IgG HRP conjugate and mouse anti-GFAP, (b) the Alexa Fluor 488 dye-labeled Fab fragment of goat anti-(mouse $IgG_1$ Fc)

antibody complex of mouse anti-GFAP, (c) Alexa Fluor 488 goat anti-mouse IgG secondary antibody and mouse anti-GFAP, and (d) a direct conjugate of the Alexa Fluor 488 dye with mouse anti-GFAP. The HRP-conjugated probes were incubated with Alexa Fluor 488 tyramide using TSA Kit #2 (Molecular Probes, Inc.) according to standard procedures. The tissue staining patterns in each case were similar and consistent with the expected staining pattern of mouse anti-GFAP and staining was essentially free of nonspecific background. The relative fluorescence intensities of staining measured by digital imaging were sequentially: 541 relative intensity units for the HRP-goat anti-(mouse IgG$_1$ Fc) complex of mouse anti-GFAP and (using the combinations indicated by the letters above): (a) 539, (b) 234, (c) 294, and (d) 255 relative intensity units.

Example 18

Staining of Live Cells by Multiple Immunolabeling Complexes

Figure 5A:
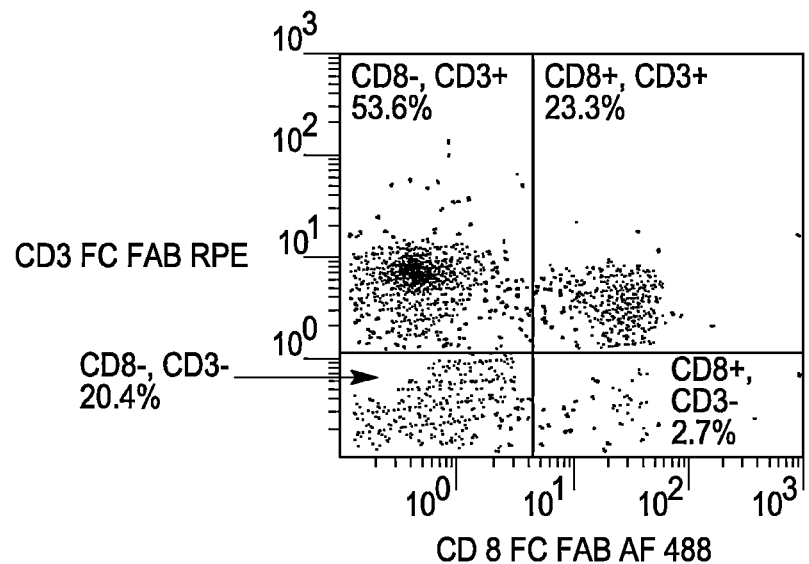
FIG. 5: Shows detection of multiple targets on T cells using a labeling reagent attached to a R-phycoerythrin (R-PE) (FIG. 5A) to detect CD3-positive T cells, a labeling reagent attached to Alexa Fluor 647 dye (FIG. 5B) to detect CD4-positive T cells and a labeling reagent attached to Alexa Fluor 488 dye (FIG. 5B) to detect CD8-positive T cells (Example 18). The CD-3 detected T cells are shown in the upper left (UL) and upper right (UR) quadrants. The relative percentages of total lymphocytes that are CD3-positive cells are 83.3% (UL+UR). The relative percentage of CD8-positive Alexa Fluor 488 dye-stained lymphocytes and CD3-positive R-PE dye-stained lymphocytes is 35.1% (UR quadrant). The lower left quadrant (LL, 20.4%) shows CD3-negative lymphocytes (i.e. non-T cells) comprised of NK cells, B cells and some monocytes. In the lower right (LR, 2.7%) region are non-T cells, which are nonspecifically stained.
FIG. 5B further shows CD3-positive T-cells subdivided into Alexa Fluor 647 dye CD4-positive and Alexa Fluor 488 dye CD8-positive. CD4-positive cells represent 50.9% of total lymphocytes (UL quadrant) and CD8-positive cells represent 24.5% of the total lymphocytes (LR quadrant). The 23.1% of cells in the LL quadrant are non-T cells, while the 1.5% of cells in UR quadrant are likely nonspecifically stained lymphocytes.
Figure 5B:
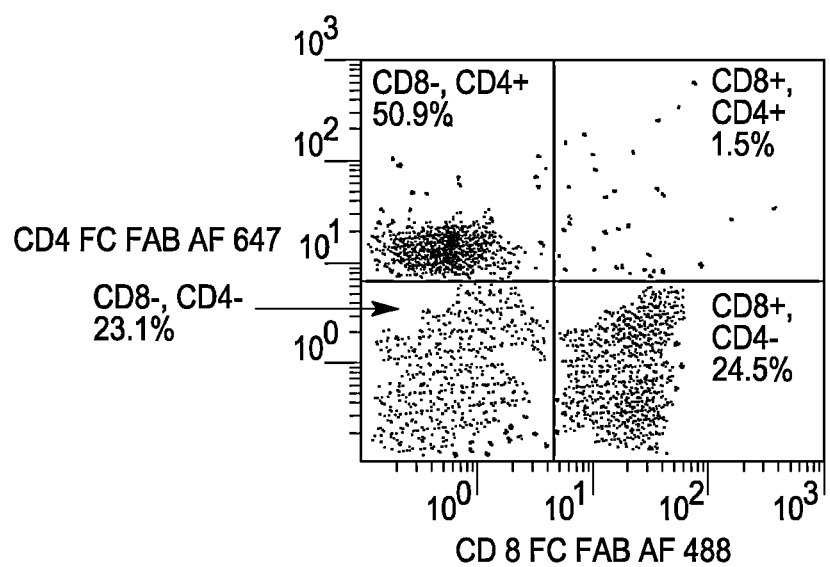

A first immunolabeling complex was prepared from an Alexa Fluor 488 dye-labeled Fab fragment of goat anti-(mouse IgG$_1$ Fc) and mouse monoclonal anti-(human CD8), a second immunolabeling complex was prepared from an R-phycoerythrin-conjugated Fab fragment of goat anti-(mouse IgG$_1$ Fc) and mouse anti-(human CD3), and a third immunolabeling complex was prepared from an Alexa Fluor 647 dye-labeled Fab fragment of goat anti-(mouse IgG$_1$ Fc) and mouse anti-(human CD4). The complexes were prepared as described in Example 8 and were each blocked with 20 µg (1.3 µL of 14.1 µg/mL) of mouse IgG for 10 minutes at room temperature. The first immunolabeling complex was added to 100 µL of whole blood and incubated for 15 min. The cells were washed with PBS and 280.5 µL of the second immunolabeling complex was added and incubated for 15 min. The cells were again washed, and 46.2 µL of the third labeling complex was added and incubated for 15 min. After the final incubation, the red blood cells were lysed with cell-lysis buffer. The cells were resuspended in 1% formaldehyde/PBS and analyzed on a FACS Vantage flow cytometer using a 488 nm argon-ion laser for excitation of the first and second immunolabeling complexes and a 633 nm red He—Ne laser for excitation of the third immunolabeling complex (FIGS. 5a, 5b). The emission band pass filters used for selective detection of the dyes are 525+/−10 nm for the Alexa Fluor 488 (CD8), 585+/−21 nm for R-PE (CD3) and 675+/−10 nm for the Alexa Fluor 647 dye (CD4). FIGS. 5a and 5b show that the instant invention can be used in a 3-color immunophenotyping experiment using peripheral blood lymphocytes. CD3-positive T cells were stained with the R-phycoerythrin-conjugated Fab fragment of goat anti-(mouse Fc) and mouse anti-(human CD3), upper left (UL) quadrant, FIG. 5a. CD4-positive cells, a T cell subset, are identified using Alexa Fluor 647 dye-labeled Fab fragment of goat anti-(mouse IgG$_1$ Fc) and mouse anti-(human CD4), UL quadrant, FIG. 5b and CD8-positive T cells, a T cell subset, were identified using Alexa Fluor 488 dye-labeled Fab fragment of goat anti-(mouse IgG$_1$ Fc) and mouse monoclonal anti-(human CD8), lower right (LR) quadrant, FIG. 5b.

Exposed antigens of live cells, including cultured cells and cells from biological fluids such as blood and cerebrospinal fluid can be simultaneously or sequentially stained by combinations of immunolabeling complexes, including antibodies to the same target labeled with two or more separately detectable immunoglobulin-binding proteins.

Example 19

The Dye-Labeled Fab Fragment of Goat Anti-(Mouse Fc) can be Utilized for the Combinatorial Labeling of Primary Antibodies, to Generate a Multitude of Colored Targets A first immuno-labeled complex was made by combining 2.5 µg Alexa Fluor 488 dye-labeled Fab fragment of goat anti-(mouse IgG$_1$ Fc) with 0.5 µg mouse anti-human CD3 (Caltag at 200 µg/mL), according to the procedure described in Example 4. A second immunolabeling complex was made by combining 5.0 µg Alexa Fluor 647 dye-labeled Fab fragment of goat anti-(mouse IgG$_1$ Fc) with 0.5 µg mouse anti-human CD3, according to the procedure in Example 4. Each complex was separately incubated at room temperature for 5 minutes, and each complex was then separately combined with an excess of mouse IgG (14.1 mg/mL) for 5 min at room temperature to capture excess unbound dye-labeled Fab fragments. The two immunolabeling complexes were then added in different percentage combinations (see Table 2) to 100 µL of washed heparinized blood. The cells were incubated with the respective combinations of complexes for 20 min on ice. The red blood cells were then lysed with a cell-lysis buffer. The cells were resuspended in 1% formaldehyde/PBS and analyzed on a FacVantage flow cytometer using a 488 nm argon 633 HeNe laser for excitation and a 530+/−10 nm band pass emission filter (FL1), and a 640 long pass filter (FL4). Five samples of different combined percentages (Table 2) were compared by flow cytometry, with signals being collected in FL1 and FL4. To determine the percentage of cells detected with each type of emission, the FL1 and FL4 intensities for each percentage combination were normalized by dividing the FL1 and FL4 channel intensities for such combinations by the intensities of the 100% Alexa Fluor 488 dye- and 100% Alexa Fluor 647 dye-labeled cells, respectively.

TABLE 2

Theoretical versus recovered dye-labeled Fab fragment of goat anti-(mouse IgG$_1$ Fc) combinatorial experiment.

| Experimentally mixed percentage of cells labeled with Alexa Fluor 488 dye-labeled Fab fragment of goat anti-(mouse IgG$_1$ Fc) | Recovered percentage of measured cells labeled with Alexa Fluor 488 dye-labeled Fab fragment of goat anti-(mouse IgG$_1$ Fc) | Experimentally mixed percentage of cells labeled with Alexa Fluor 647 dye-labeled Fab fragment of goat anti-(mouse IgG$_1$ Fc) | Recovered percentage of measured cells labeled with Alexa Fluor 647 dye-labeled Fab fragment of goat anti-(mouse IgG$_1$ Fc) |
|---|---|---|---|
| 100% | 100% | 0% | 0% |
| 75% | 81% | 25% | 14% |
| 50% | 63% | 50% | 38% |
| 25% | 35% | 75% | 73% |
| 0% | 0% | 100% | 100% |

Example 20

The Immunolabeling Complex can be Used to Detect Antigens on a Western Blot

Bovine heart mitochondria were isolated (Hanson et al., Electrophoresis 22, 950 (2001)). The isolated mitochondria were resuspended to ~10 mg/mL in 100 mM Tris-HCl, pH 7.8, 1 mM phenylmethylsulfonyl fluoride (a protease inhibitor), 2% SDS and insoluble material was removed by centrifugation for 10 minutes at 10,000×g in a tabletop centrifuge. The protein concentration of the lysate was checked by the BCA assay (Pierce, Rockford, Ill.). Samples for gel electrophoresis were prepared by mixing lysate, water, and loading buffer to the appropriate concentrations (final concentration of loading buffer in samples: 58 mM Tris/HCl, 10% glycerol, 2% SDS, 0.02 mg/mL bromphenol blue, 50 mM DTT, pH 8.6). The samples were then heated to 90° C. for 5 minutes before loading on the gel and separated on a 13% SDS-PAGE gel. Two-fold serial dilution of the extracts ranging from 8 μg of extract down to 0.03 μg were loaded on the SDS-PAGE gel. The proteins were transferred to PVDF membrane for 1.5 hours using a semi-dry transfer system according to manufacturer's directions (The W.E.P. Company, Concord, Calif.). The PVDF membrane was blocked for 1 hour in 5% milk.

Immunolabeling complexes were made with mouse monoclonal antibodies that recognize two different mitochondrial proteins. Alexa Fluor 647 dye-labeled Fab fragment of goat anti-(mouse $IgG_1$ Fc) (5 μL of a 1 mg/mL stock, prepared as in Example 4) was incubated with 21 μL (0.88 mg/mL) mouse anti-(CV-alpha) and Alexa Fluor 488 dye-labeled Fab fragment of goat anti-(mouse $IgG_1$ Fc) (5 μL of a 1 mg/mL stock, prepared as in Example 4) was incubated with 19 μL (0.88 mg/mL) mouse anti-(CIII-core2) (Molecular Probes, Eugene, Oreg.). Following a 30 minute incubation, 25 μL of a 14.1 mg/mL stock of unlabeled mouse IgG was added to each tube. The immunolabeling complexes were then mixed together and brought up to 5 mL in 5% milk. The blot was incubated with the mixture of immunolabeling complexes for 1 hour at room temperature. The blot was washed twice for 5 seconds each with PBST (PBS with 0.1% Tween) and once with PBST for 15 minutes. The blot was air dried and imaged on an EG&G Wallac Imager with the appropriate filters. The Western blot revealed two distinct bands of the appropriate molecular weight. The Western blot also showed that no cross-labeling of the antibodies occurred and the detection limit was 125 ng.

Example 21

High-Throughput Screening of Hybridomas for Identifying High Affinity and High IgG Producers Microplate wells containing both a fluorescent labeled antigen of one fluorescent color label and fluorescently labeled Fab fragments of goat anti-(mouse Fc) of a different fluorescent color made by the method described in Example 4 and 5. Hybridoma supernatant is harvested and added to the wells. If the hybridoma are producing the desired antibody, i.e. antibodies that bind to the labeled antigen, polarization of the florescence corresponding to the labeled antigen will allow visualization of those wells containing antigen specific antibody. In addition, the amount of IgG that the hybridomas produce, can be simultaneously identified by polarization of the fluorescence corresponding to the labeled Fab fragments. This method thus allows for both quantitation of the amount of antibody present in a specific amount of hybridoma supernatant and the affinity of the monoclonal antibodies for the antigen.

The reagents employed in the preceding examples are commercially available or can be prepared using commercially available instrumentation, methods, or reagents known in the art or whose preparation is described in the examples. It is evident from the above description and results that the subject invention is greatly superior to the presently available methods for determining the presence of a target in a biological sample. The subject invention overcomes the shortcomings of the currently used methods by allowing small quantities of antibodies to be labeled and in unlimited media while maintaining specificity and sensitivity. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference to the same extent as if each individual publication, patent or patent application was specifically and individually indicated to be incorporated by reference.

What is claimed is:

1. A method of manufacturing an isolated labeling reagent, wherein said method comprises the steps of:
    a) cleaving an intact anti-region antibody with an enzyme to generate Fab fragments;
    b) isolating said anti-region Fab fragments of step a);
    c) contacting a matrix comprising intact immunoglobulin proteins or fragments that selectively bind anti-region Fab fragments with a solution comprising said anti-region fragments of step b) wherein said anti-region Fab fragments are immobilized on said matrix;
    d) contacting said matrix of step c) with a solution comprising a fluorophore label that contains a reactive group;
    e) washing said matrix of step d) to remove unbound label, and;
    f) eluting said labeling reagent from said matrix whereby said isolated labeling reagent is manufactured.

2. The method according to claim 1, wherein said anti-region Fab fragment are selected from the group consisting of anti-Fc antibody fragment, anti-kappa light chain antibody fragment, anti-lambda light chain antibody fragment, and a single chain variable protein fragment.

3. The method according to claim 2, wherein said fluorophore is selected from the group consisting of a coumarin, a xanthene, a cyanine, a pyrene, a borapolyazaindacene, an oxazine and derivatives thereof.

4. A method of manufacturing an isolated labeling reagent, wherein said method comprises the steps of:
    a) contacting a matrix comprising intact immunoglobulin proteins or fragments thereof that selectively bind non-antibody proteins with a solution comprising said non-antibody proteins wherein said non-antibody proteins are immobilized on said matrix;
    b) contacting said matrix of step a) with a solution comprising a fluorophore label that contains a reactive group;
    c) washing said matrix to remove unbound label, and;

d) eluting said labeling reagent from said matrix whereby said isolated labeling reagent is manufactured that comprises a fluorophore label.

5. The method according to claim 4, wherein said non-antibody protein is selected from the group consisting of protein G, protein A, protein L, lectin, and derivatives thereof.

6. The method according to claim 5, wherein said fluorophore is selected from the group consisting of a coumarin, a xanthene, a cyanine, a pyrene, a borapolyazaindacene, an oxazine and derivatives thereof.

7. An isolated labeling reagent made by a process comprising:
   a) cleaving an intact anti-region antibody with an enzyme to generate Fab fragments;
   b) isolating said anti-region Fab fragments of step a);
   c) contacting a matrix comprising intact immunoglobulin proteins or fragments thereof that specifically bind anti-region Fab fragments with a solution comprising said anti-region Fab fragments of step b) wherein said anti-region Fab fragments are immobilized;
   d) contacting said matrix of step c) with a solution comprising a fluorophore label that contains a reactive group;
   e) washing said matrix to remove unbound label, and;
   f) eluting said labeling reagent from said matrix whereby said labeling reagent is manufactured comprising a label and being isolated from other proteins or fragments thereof.

8. The labeling reagent according to claim 7, wherein said anti-region Fab fragment is selected from the group consisting of anti-Fc antibody fragment, anti-kappa light chain antibody fragment, anti-lambda light chain antibody fragment, and a single chain variable protein fragment.

9. The labeling reagent according to claim 8, wherein said fluorophore is selected from the group consisting of a coumarin, a xanthene, a cyanine, a pyrene, a borapolyazaindacene, an oxazine and derivatives thereof.

* * * * *